United States Patent
Magee

(10) Patent No.: US 9,750,916 B2
(45) Date of Patent: Sep. 5, 2017

(54) HUMIDIFIED GAS DELIVERY SYSTEM

(75) Inventor: Ciarán Dominic Magee, Londonderry (GB)

(73) Assignee: ARMSTRONG MEDICAL LIMITED, Londonderry (GB)

( * ) Notice: Subject to any disclaimer, the term of this patent is extended or adjusted under 35 U.S.C. 154(b) by 554 days.

(21) Appl. No.: 14/240,730

(22) PCT Filed: Aug. 23, 2012

(86) PCT No.: PCT/EP2012/066420
§ 371 (c)(1),
(2), (4) Date: May 5, 2014

(87) PCT Pub. No.: WO2013/026901
PCT Pub. Date: Feb. 28, 2013

(65) Prior Publication Data
US 2015/0108670 A1  Apr. 23, 2015

(30) Foreign Application Priority Data
Aug. 23, 2011 (GB) .................................. 1114580.2

(51) Int. Cl.
*A61M 16/10* (2006.01)
*A61M 16/08* (2006.01)
(Continued)

(52) U.S. Cl.
CPC .... *A61M 16/1045* (2013.01); *A61M 16/0875* (2013.01); *A61M 16/108* (2014.02);
(Continued)

(58) Field of Classification Search
CPC .............. A61M 16/0875; A61M 16/16; A61M 16/108; A61M 16/109; A61M 16/1095;
(Continued)

(56) References Cited

U.S. PATENT DOCUMENTS 638,236 A * 12/1899 Gold ........................ H01C 3/14
338/286
1,171,059 A * 2/1916 Loguin .................... H01C 3/20
338/296
(Continued)

FOREIGN PATENT DOCUMENTS

EP          1 352 670 A1   10/2003
EP          2 055 336 A1    5/2009
(Continued)

OTHER PUBLICATIONS

PCT International Search Report for Internation Application PCT/EP2012/066420, Jul. 3, 2013, 7 pages.

*Primary Examiner* — Charles Bushey
(74) *Attorney, Agent, or Firm* — Karen S. Canady; canady + lortz LLP

(57) ABSTRACT

This invention relates to a method for delivering humidified gas to a user or patient during respiratory gas ventilation support, such as, but not limited to, mechanical ventilation, continuous positive airway pressure breathing, and bi-directional positive airway pressure breathing; the method comprising the steps of heating a humidified gas from a humidified gas reservoir; transferring the heated humidified gas to a patient; receiving expired gas from a patient; heating the expired gas; and transferring the heated expired gas to a gas outlet; wherein the humidified gas and the expired gas are heated to different temperatures. Also disclosed is a humidified gas delivery system, which finds utility as a breathing circuit of a respiratory gas humidification system by delivering humidified gases to a user or patient during mechanical ventilation, continuous positive airway pressure breathing, bi-directional positive airway pressure breathing, or other mode of respiratory support provided to users or patients.

20 Claims, 8 Drawing Sheets

(51) Int. Cl.
*A61M 16/16* (2006.01)
*F16L 53/00* (2006.01)

(52) U.S. Cl.
CPC ...... *A61M 16/109* (2014.02); *A61M 16/1085* (2014.02); *A61M 16/1095* (2014.02); *A61M 16/16* (2013.01); *A61M 16/167* (2014.02); *F16L 53/004* (2013.01); *A61M 16/0833* (2014.02); *A61M 2205/3653* (2013.01)

(58) Field of Classification Search
CPC ............ A61M 16/167; A61M 16/1045; A61M 16/1085; A61M 2205/3653; A61M 16/0833; F16L 53/004; F16L 53/008
USPC ........................................... 261/142, DIG. 65
See application file for complete search history.

(56) References Cited

U.S. PATENT DOCUMENTS

| | | | | |
|---|---|---|---|---|
| 2,957,154 | A * | 10/1960 | Strokes | H05B 3/44 219/553 |
| 3,551,643 | A * | 12/1970 | Pricenski et al. | F24H 1/121 219/546 |
| 4,207,457 | A * | 6/1980 | Haglund | H05B 3/44 219/546 |
| 4,401,883 | A * | 8/1983 | Watson | H05B 3/64 219/536 |
| 5,529,060 | A | 6/1996 | Salmon et al. | |
| 8,063,343 | B2 * | 11/2011 | McGhin | A61M 16/1075 128/203.17 |
| 2002/0124847 | A1 | 9/2002 | Smith | |
| 2004/0250815 | A1 * | 12/2004 | Scott | A61M 16/08 128/204.17 |
| 2008/0105257 | A1 | 5/2008 | Klasek et al. | |
| 2010/0206308 | A1 * | 8/2010 | Klasek | A61M 16/0066 128/203.27 |
| 2011/0108031 | A1 * | 5/2011 | Korneff | A61M 16/0875 128/203.27 |
| 2012/0152247 | A1 * | 6/2012 | Labollita | A61M 16/0875 128/203.27 |
| 2013/0263845 | A1 * | 10/2013 | Arcilla | A61M 11/005 128/200.14 |
| 2013/0284169 | A1 * | 10/2013 | Foote | A61M 16/1075 128/203.14 |

FOREIGN PATENT DOCUMENTS

| | | |
|---|---|---|
| EP | 2 119 466 A1 | 11/2009 |
| WO | WO 97/18001 A1 | 5/1997 |
| WO | WO 2008/055307 A1 | 5/2008 |

* cited by examiner

DETAIL A
SCALE 1 : 1

HUMIDIFIED GAS DELIVERY SYSTEM

This invention relates to a method for delivering humidified gas to a user or patient during respiratory gas ventilation support, such as, but not limited to, mechanical ventilation, continuous positive airway pressure breathing, and bi-directional positive airway pressure breathing. The invention also relates to a humidified gas delivery system for incorporation in a breathing circuit of a respiratory gas humidification system by delivering humidified gas to a user or patient during respiratory gas ventilation support such as, but not limited to, mechanical ventilation, continuous positive airway pressure breathing, bi-directional positive airway pressure breathing, or other mode of respiratory support provided to users or patients.

BACKGROUND TO THE INVENTION

Respiratory gas humidification is a method of heating and humidifying respiratory gas for a user or patient, particularly the heating and humidifying of respiratory gas to be inhaled by the user or patient requiring respiratory gas ventilation support, possibly over a prolonged period of time. Respiratory gas humidification is necessary to compensate for losses of heat and moisture when natural airway passages of the user or patient are bypassed or somehow otherwise restricted as necessitated by the equipment used in providing a secure airway path into and from the patient's lungs to conduct respiratory gas ventilation support. Respiratory gas humidification could reduce or avoid clinical complications, such as pulmonary infection, physical damage of lung tissue, and/or debilitation of lung function.

Generally, there are two known methods of respiratory gas humidification, namely, active respiratory gas humidification, and passive respiratory gas humidification.

Active respiratory gas humidification typically uses gas and water transporting conduits, and/or gas and water vapour transporting conduits, provided with a gas-heating means and connected to a water-vapour-generating means such as a humidifier control unit and water vessel containing the water for evaporation. Water vessels of the prior art, commonly called humidification chambers, and such inspiratory and expiratory conduits of the prior art, under certain conditions, are known to cause unintentional condensing of evaporated water; whereby the condensed water unintentionally accumulates in the inspiratory and/or expiratory conduits. Unintentional accumulation of condensed water poses a risk to patient respiration, due to potential occlusion of the gases pathway to and/or from the patient's lungs; and/or under-humidification of inhalatory breathing gases.

Passive respiratory gas humidification is conducted without, and independent from, any external energy source or external water supply. Typically, passive respiratory gas humidifiers act as heat and moisture Exchangers (HME) by withdrawing heat and moisture from expired gas from a user or patient, and supplying the heat and moisture to gas to be inspired by the user or patient.

The present invention relates to a humidified gas delivery system for use in active respiratory gas humidification, and ensures that a user or patient is supplied with conditioned respiratory gas. In active humidifying methods, moisture and heat is input to respiratory gas prior to inhalation by the user or patient. Performance data and safety-related requirements for active respiratory gas humidifiers are specified by the standard ISO 8185. According to that standard, the minimum water content of inspired respiratory gas is about 33 mg/L of gas flow and the maximum respiratory gas temperature for inhalation is about 42° C.

In order to deliver gas, for example humidified respiratory gas, to a user or patient, flexible piping, typically having a length of about 1 to about 2 meters and having a wall thickness in the range of about 0.4 to about 2 mm, is used to deliver gas from a gas supply means to the user or patient (inspiratory conduit), and to deliver gas from the user or patient (expiratory conduit) to an outlet (or back to the gas supply in the case of a mechanical ventilator or other gas flow generating or receiving means).

The moisture content of humidified respiratory gas is raised, which is achieved by artificially increasing the amount of water vapour in the respiratory gas. Optimally, the relative humidity of the respiratory gas is 100% when inhaled by the patient or user. Artificial increase of the amount of water vapour in the respiratory gas is achieved by the use of a humidifier—a device, which enriches the respiratory gas with water vapour, for example, whereby a flow of respiratory gas (from a gas supply) is guided in the presence of a reservoir of water. The reservoir of water is heated to facilitate water evaporation and the production of water vapour, which water vapour is transported from the surface of the water in the reservoir to the inspiratory conduit by the flow of respiratory gas.

However, the water vapour transported by a humidified gas of high, for example 100% or greater, relative humidity is more likely to condense and accumulate at the inner walls of the inspiratory conduit—a process known as "rain out". Consequently, the inspiratory circuit must be regularly drained to remove the accumulated liquid to circumvent the accumulated liquid reaching the lungs of the user or the patient.

Similarly, the expiratory conduit, which delivers gas to an outlet, will deliver humidified gas of high, for example >100%, relative humidity from the lungs of the user or patient, and water vapour transported by the expired gas is likely to condense and accumulate in the expiratory circuit, requiring regular draining, particularly in the case of an expiratory conduit connected to a mechanical ventilator or other gas flow generating or receiving means.

The prior art teaches that the inspiratory and expiratory conduits incorporate heating elements to heat the respiratory gas and simultaneously heat the conduit walls to a suitable temperature, and to maintain a constant temperature across the entire length of both of the inspiratory and expiratory conduits, in order to reduce condensation.

SUMMARY OF THE INVENTION

According to a first aspect of the present invention, there is provided a method for delivering humidified gas to a patient, the method comprising the steps of:
 (a) heating a humidified gas from a humidified gas reservoir;
 (b) transferring the heated humidified gas to a patient;
 (c) receiving expired gas from a patient;
 (d) heating the expired gas; and
 (e) transferring the heated expired gas to a gas outlet;
wherein the humidified gas and the expired gas are heated to different temperatures.

Optionally, the method comprises the steps of: (a) heating a humidified gas; (b) transferring the heated humidified gas to a patient; (c) heating expired gas from a patient; and (d) transferring the heated expired gas from the patient; wherein the humidified gas and the expired gas are heated to different temperatures.

According to a second aspect of the present invention, there is provided a humidified gas delivery system, the system comprising:
 (a) an inspiratory conduit for transferring a humidified gas from a humidified gas reservoir to a patient;
 (b) means for heating the inspiratory conduit;
 (c) an expiratory conduit for transferring expired gas from a patient to a gas outlet; and
 (d) means for heating the expiratory conduit;
wherein the respective heating means are each arranged to heat the humidified gas and the expired gas to different temperatures.

Optionally, the system comprises: (a) an inspiratory conduit having proximal and distal ends for transferring a humidified gas to a patient; (b) means for heating the inspiratory conduit; (c) an expiratory conduit having proximal and distal ends for transferring expired gas from a patient; and (d) means for heating the expiratory conduit; wherein the respective heating means are each arranged to heat the humidified gas and the expired gas to different temperatures.

In a particular embodiment, the inspiratory conduit can comprise a pipe, optionally a flexible pipe, for transporting gases for inhalation, optionally from the humidified gas reservoir to the patient. The expiratory conduit, in a particular embodiment, can comprise a flexible pipe for transporting exhaled gases from the patient to the gas outlet. The inspiratory conduit has proximal and distal ends. Additionally, the expiratory conduit has proximal and distal ends. Each proximal end is, in use, the end at or adjacent a patient. Each distal end is, in use, the end at or adjacent a gas outlet.

Optionally, a conduit connection is provided, in use, at or adjacent the proximal end of the inspiratory conduit; and, in use, at or adjacent the proximal end of the expiratory conduit. Optionally, the conduit connection is, in use, in fluid communication with each of the inspiratory and expiratory conduits. Optionally, the conduit connection is, in use, in fluid communication with a delivery device, such as a facemask or nasal mask. Optionally or additionally, the delivery device, such as a face mask or nasal mask, is, in use, in fluid communication with the lungs of the patient, for example, is, in use, mounted to the face of the patient or to a tracheal tube, optionally located in the oral cavity or nasal orifice of the patient. Further optionally, the delivery device is, in use, mounted to a tracheostomy tube located in a tracheotomy stoma of the patient. Optionally, the conduit connection and/or the delivery device is/are adapted to allow bi-directional and/or uni-directional passage of gas, optionally humidified gas, therethrough. Further optionally, the conduit connection and/or the delivery device is/are adapted to allow bi-directional and/or uni-directional passage of gas, optionally humidified gas, between the tracheo-bronchial bifurcation of the patient and each of the inspiratory and/or expiratory conduits of the humidified gas delivery system. Still further optionally, the conduit connection and/or the delivery device is/are adapted to allow bi-directional and/or uni-directional passage of gas, optionally humidified gas, therethrough, such that a humidified gas delivery circuit, optionally a closed humidified gas delivery circuit, is established. Optionally, the humidified gas delivery circuit, optionally the closed humidified gas delivery circuit, transfers humidified gases for inhalation and humidified gases for exhalation.

Optionally, the expired gas is heated to between about 34° C. and about 44° C. Further optionally, the expired gas is heated to at least 38° C. Still further optionally, the expired gas is heated to at least 42° C. Preferably, the expired gas is heated to about 44° C. Optionally, the expired gas is heated to any suitable temperature, such that the expired gas is heated to about 44° C. at or adjacent the distal end of the expiratory conduit, at or adjacent the gas outlet. Optionally, the expired gas is heated to a temperature from about 34° C. (at or adjacent the proximal end of the expiratory conduit) to about 44° C. (at or adjacent the distal end of the expiratory conduit). Further optionally, the expired gas is heated to about 34° C. when received at or adjacent the patient (at or adjacent the proximal end of the expiratory conduit). Optionally or additionally, the expired gas is heated to about 44° C. when received at or adjacent the gas outlet (at or adjacent the distal end of the expiratory conduit). Optionally, the expired gas is heated to about 34° C. when received at or adjacent the patient (at or adjacent the proximal end of the expiratory conduit), and the expired gas is heated to a temperature to about 44° C. when received at or adjacent the gas outlet (at or adjacent the distal end of the expiratory conduit). The expired gas can be heated sequentially (in uniform or non-uniform increments) from about 34° C. when received at or adjacent the patient and heated to a temperature of about 44° C. when received at or adjacent the gas outlet. Optionally, the expired gas is heated to a temperature such that the relative humidity of the expired gas is less than 90%, optionally less than 80%, further optionally less than 70%, still further optionally less than 60%, still further optionally less than 55%; optionally when received at or adjacent the gas outlet (at or adjacent the distal end of the expiratory conduit).

By "relative humidity" is meant a measure of the amount of water in a mixture of gas and water vapour, optionally at a given gas temperature and atmospheric pressure, optionally at constant atmospheric pressure, optionally expressed as a percentage of the maximum amount of water vapour within the gas at the given gas temperature and atmospheric pressure. For the purposes of this specification, the term "relative humidity" is intended to mean a measure of the amount of water vapour in a mixture of the humidified gas from the humidified gas reservoir and water vapour; and/or a measure of the amount of water vapour in a mixture of the gas from the patient, optionally at a constant atmospheric pressure, optionally expressed as a percentage. For the purposes of this specification, atmospheric pressure understood to be about 980 to about 1040 millibars. By 'ambient conditions' is meant ambient temperature of about 21° C. at between about 40 and about 65% relative humidity combined with ambient airflow speed of less than about 5 cm/second.

Optionally, the heated humidified gas is transferred to the patient at about 30 to about 50 mg/L, optionally about 33 to about 46 mg/L, preferably about 43 to about 45 mg/L, more preferably about 44 mg/L; optionally when received at or adjacent the patient (at or adjacent the proximal end of the inspiratory conduit).

By 'patient' is meant any user to whom the humidified gas is transferred from the humidified gas reservoir. Optionally, the humidified gas is transferred from the humidified gas reservoir to the airway passages of the patient, optionally to the pulmonary tracheo-bronchial bifurcation, further optionally the Carina of the lungs, of the patient.

Optionally, the heated expired gas is transferred to the gas outlet at less than about 55 mg/L, optionally less than 50 mg/L, preferably about 44 mg/L; optionally when received at or adjacent the gas outlet (at or adjacent the distal end of the expiratory conduit).

Optionally or additionally, the humidified gas from the humidified gas reservoir is heated to between about 28° C.

and about 40° C. Further optionally, the humidified gas from the humidified gas reservoir is heated to about 32° C. Still further optionally, the humidified gas from the humidified gas reservoir is heated to about 36° C. Preferably, the humidified gas from the humidified gas reservoir is heated to about 37° C. Optionally, when the humidified gas from the humidified gas reservoir is heated to between about 34° C. to about 40° C., the expired gas is heated to about 3° C. greater than the temperature of the humidified gas from the humidified gas reservoir. Optionally, the humidified gas from the humidified gas reservoir is heated to about 37° C. at or adjacent the gas reservoir (at or adjacent the distal end of the inspiratory conduit). Optionally, the humidified gas from the humidified gas reservoir is heated to a temperature from about 28° C. to about 40° C. Further optionally, the humidified gas from the humidified gas reservoir is heated to about 37° C. when received at or adjacent the gas reservoir (at or adjacent the distal end of the inspiratory conduit). Optionally or additionally, the humidified gas from the humidified gas reservoir is heated to about 40° C. when received at or adjacent the patient (at or adjacent the proximal end of the inspiratory conduit). Optionally, the humidified gas from the humidified gas reservoir is heated to about 37° C. when received at or adjacent the gas reservoir (at or adjacent the distal end of the inspiratory conduit), and the humidified gas from the humidified gas reservoir is heated to a temperature to about 40° C. when received at or adjacent the patient (at or adjacent the proximal end of the inspiratory conduit). The humidified gas can be heated sequentially (in uniform or non-uniform increments) from about 37° C. when received at or adjacent the gas reservoir and heated to a temperature of about 40° C. when received at or adjacent the patient. Optionally, the humidified gas from the humidified gas reservoir is heated to a temperature such that the relative humidity of the humidified gas from the humidified gas reservoir is at least 50%, optionally at least 60%, further optionally at least 70%, still further optionally at least 80%, still further optionally at least 90%; optionally when received at or adjacent the patient (at or adjacent the proximal end of the inspiratory conduit).

Optionally, the inspiratory conduit is thermally conductive. Further optionally, the inspiratory conduit is formed from a thermally conductive material. Optionally, the temperature of the external surface of the inspiratory conduit; which is optionally in contact with ambient conditions and under mechanical ventilation flow pattern of, for example, about 500 mL tidal volume at about 18 breaths per minute; is about 33° C. to about 40° C., optionally about 34° C. to about 37° C.; optionally when the temperature is measured at a location at about 5% to about 10% of the total length of the inspiratory conduit from the distal end of the inspiratory conduit.

Optionally, the expiratory conduit is thermally conductive. Further optionally, the expiratory conduit is formed from a thermally conductive material. Optionally, the temperature of the external surface of the expiratory conduit; which is optionally in contact with ambient conditions and under mechanical ventilation flow pattern of, for example, about 500 mL tidal volume at about 18 breaths per minute; is about 38° C. to about 44° C., optionally about 42° C. to about 44° C.; optionally when the temperature is measured at a location at about 5% to about 10% of the total length of the expiratory conduit from the distal end of the expiratory conduit.

Optionally, the humidified gas from the humidified gas reservoir is heated using an electrically conductive resistor. Optionally or additionally, the expired gas from a patient is heated using an electrically conductive resistor. Optionally, the resistor has a resistivity of about $0.1 \times 10^{-3}$ $\Omega$m (0.1 milliohmmeters) to about $25.0 \times 10^{-3}$ $\Omega$m (25.0 milliohmmeters), optionally at about 20° C.

Optionally, the power dissipated by the resistor is from about 18 to about 42 watts. Optionally, the humidified gas from the humidified gas reservoir is heated using an electrically conductive resistor, wherein the power dissipated by the resistor is from about 18 to about 34 watts, optionally from about 20 to about 30 watts, further optionally from about 22 to about 28 watts. Optionally or additionally, the expired gas from a patient is heated using an electrically conductive resistor, wherein the power dissipated by the resistor is from about 28 to about 42 watts, optionally from about 30 to about 40 watts, further optionally from about 32 to about 38 watts.

Optionally, the resistor has an electrical resistance of no more than 25 ohms, optionally at about 20° C. Optionally, the humidified gas from the humidified gas reservoir is heated using an electrically conductive resistor having an electrical resistance of about 13 to about 20 ohms, optionally about 15 to about 17 ohms, preferably about 16 ohms, optionally at about 20° C. Optionally, the expired gas is heated using an electrically conductive resistor having an electrical resistance of about 10 to about 16 ohms, optionally about 11 to about 14 ohms, preferably about 12 ohms, optionally at about 20° C.

Optionally, current is supplied to the or each resistor in a continuous or semi-continuous manner.

Optionally, current is supplied to the or each resistor when the humidified gas is below a first temperature. Further optionally, current is not supplied to the resistor when the humidified gas is above a second temperature. Still further optionally, current is supplied to the resistor when the humidified gas is below a first temperature; and current is not supplied to the resistor when the humidified gas is above a second temperature; wherein the first and second temperatures are the same or different temperatures. Optionally, the humidified gas from the humidified gas reservoir is heated using an electrically conductive resistor, wherein current is supplied to the resistor when the humidified gas is below a first temperature of about 28° C., optionally about 31° C., further optionally about 34° C., preferably about 37° C.; optionally when received at or adjacent the patient (at or adjacent the proximal end of the inspiratory conduit). Optionally, the humidified gas from the humidified gas reservoir is heated using an electrically conductive resistor, wherein current is not supplied to the resistor when the humidified gas is above a second temperature of about 40° C., optionally about 42° C., further optionally about 44° C.; optionally when received at or adjacent the patient (at or adjacent the proximal end of the inspiratory conduit). Optionally or additionally, the humidified gas from the humidified gas reservoir is heated using an electrically conductive resistor, wherein current is not supplied to the resistor when the difference in the temperature of the humidified gas when measured at or adjacent the humidified gas reservoir (at or adjacent the distal end of the inspiratory conduit), and the temperature of the humidified gas when measured at or adjacent the patient (at or adjacent the proximal end of the inspiratory conduit), is more than 3° C. Optionally, the expired gas from the patient is heated using an electrically conductive resistor, wherein current is supplied to the resistor when current is supplied to the resistor in the inspiratory conduit. Optionally, the expired gas is heated using an electrically conductive resistor; wherein current is not supplied to the resistor when current is not supplied to the resistor in the inspiratory conduit.

Optionally, the inspiratory conduit is arranged to allow the passage of the heated humidified gas therethrough. Further optionally, the inspiratory conduit comprises a hollow cylindrical tube. Still further optionally, the inspiratory conduit comprises a hollow cylindrical tube having open proximal and distal ends.

Further optionally, an internal surface of the inspiratory conduit comprises a smooth surface, along all or any part of the inside of the conduit length. Further optionally or additionally, the internal diameter of the inspiratory conduit is about 10 to about 32 mm, optionally about 15 to about 26 mm, further optionally about 20 to 24 mm, preferably about 20 to about 22 mm. Further optionally, an internal surface of the expiratory conduit comprises a smooth surface, along all or any part of the inside of the conduit length. Further optionally or additionally, the internal diameter of the expiratory conduit is about 10 to about 32 mm, optionally about 15 to about 26 mm, further optionally about 20 to 24 mm, preferably about 20 to about 22 mm.

Optionally, the inspiratory conduit comprises circumferential recesses, optionally a plurality of repeated circumferential recesses, along at least a portion of the inspiratory conduit. Further optionally, the inspiratory conduit comprises circumferential recesses, optionally a plurality of repeated circumferential recesses, along at least a portion of the inner surface of the inspiratory conduit. Optionally or additionally, the expiratory conduit comprises circumferential recesses, optionally a plurality of repeated circumferential recesses, along at least a portion of the expiratory conduit. Further optionally, the expiratory conduit comprises circumferential recesses, optionally a plurality of repeated circumferential recesses, along at least a portion of the inner surface of the expiratory conduit.

Optionally, the inspiratory conduit is arranged to receive a resistor. Further optionally, the inspiratory conduit is arranged to receive a resistor within the lumen thereof. Optionally or additionally, the expiratory conduit is arranged to receive a resistor. Further optionally, the expiratory conduit is arranged to receive a resistor within the lumen thereof. Optionally, the inspiratory conduit further comprises means to secure the resistor thereto. Further optionally, the inspiratory conduit further comprises means to secure the resistor within the lumen thereof. Optionally or additionally, the expiratory conduit further comprises means to secure the resistor thereto. Further optionally, the expiratory conduit further comprises means to secure the resistor within the lumen thereof.

Optionally, the resistor is a wire. Optionally, the wire has a constant cross-sectional dimension. Optionally, the wire has a resistance of about 1.5 to about 3.0 ohms per meter length, optionally about 1.75 to about 2.5 ohms per meter length, preferably 2.0 ohms per meter length. Optionally, the wire is at least partially surrounded by an electrically non-conductive polymeric material. Optionally, the polymeric material is selected from polyolefins and polyamides. Further optionally, the polymeric material is selected from polypropylene and nylon. Optionally, the thickness of the electrically non-conductive polymeric material is about 0.2 to about 2 mm, preferably about 0.4 to about 1 mm.

Optionally, the resistor is formed from a metal or an alloy; although one skilled in the art may select any suitable material having the required resistivity. Optionally, the resistor is formed from a metal or an alloy selected from Aluminum; Brass; Carbon, optionally amorphous Carbon; Constantan; Copper; Iron; Manganin; Molybdenum; Nichrome; Nickel; Platinum; Stainless steel; Steel; Tungsten; and Zinc.

Optionally, in use, the resistor, optionally the wire, is positioned within the inspiratory conduit. Further optionally, in use, the resistor, optionally the wire, is positioned within the lumen of the inspiratory conduit. Optionally, at least part of the wire is arranged to extend circumferentially within at least a portion of the lumen of the inspiratory conduit. Optionally, or additionally, at least part of the wire is arranged to extend across the lumen of the inspiratory conduit; optionally across a transverse cross-section of the lumen of the inspiratory conduit. Preferably, at least part of the wire is arranged to extend circumferentially within at least a portion of the lumen and at least part of the wire is arranged to extend across the lumen of the inspiratory conduit; optionally across a transverse cross-section of the lumen of the inspiratory conduit. Optionally, the wire is formed from a series of at least two segments, wherein each segment, at least part of the wire is arranged to extend circumferentially within at least a portion of the lumen and at least part of the wire is arranged to extend across the lumen of the inspiratory conduit; optionally across a transverse cross-section of the lumen of the inspiratory conduit.

Optionally, in use, the resistor, optionally the wire, is positioned within the expiratory conduit. Further optionally, in use, the resistor, optionally the wire, is positioned within the lumen of the expiratory conduit. Optionally, at least part of the wire is arranged to extend circumferentially within at least a portion of the lumen of the expiratory conduit. Optionally, or additionally, at least part of the wire is arranged to extend across the lumen of the expiratory conduit; optionally across a transverse cross-section of the lumen of the expiratory conduit. Preferably, at least part of the wire is arranged to extend circumferentially within at least a portion of the lumen and at least part of the wire is arranged to extend across the lumen of the expiratory conduit; optionally across a transverse cross-section of the lumen of the expiratory conduit. Optionally, the wire is formed from a series of at least two segments, wherein each segment, at least part of the wire is arranged to extend circumferentially within at least a portion of the lumen and at least part of the wire is arranged to extend across the lumen of the expiratory conduit; optionally across a transverse cross-section of the lumen of the expiratory conduit.

Optionally, each segment has a serpentine form. Further optionally, each segment is shaped in the form of the letter "S". Optionally, each segment has a first portion having distal and proximal ends, a middle portion having distal and proximal ends, a second portion having distal and proximal ends, and a connector having distal and proximal ends. Optionally, the first portion is substantially curvilinear in form. Optionally, the middle portion is substantially linear in form. Optionally, the second portion is substantially curvilinear in form. Optimally, the connector is substantially linear in form. Optionally, the first portion is substantially curvilinear in form, the proximal end of which first portion is connected to the distal end of the middle portion, which middle portion is substantially linear in form; and the proximal end of the middle portion is connected to the distal end of the second portion, which second portion is substantially curvilinear in form. Optionally, the connector is substantially linear in form and extends between the distal end of a first portion of a first segment of the wire and the proximal end of a second portion of an adjacent segment of the wire.

Optionally, each segment is deformed with respect to the longitudinal axis of the inspiratory conduit. Optionally, the distal end of a first portion of a first segment of the wire and the proximal end of a second portion of an adjacent segment of the wire are spaced apart with respect to the longitudinal axis of the inspiratory conduit. Optionally, the wire is formed from a series of at least two segments adjacently arranged with respect to the longitudinal axis of the inspiratory conduit.

Optionally, the inspiratory conduit comprises more than one resistor. Further optionally, the inspiratory conduit comprises more than one wire. Optionally, the inspiratory conduit comprises more than one wire, wherein each wire is positioned coaxially with respect to the longitudinal axis of the inspiratory conduit. Optionally, the inspiratory conduit comprises more than one wire, wherein each wire is positioned coaxially, and staggered relative to another wire, with respect to the longitudinal axis of the inspiratory conduit. Optionally, the inspiratory conduit comprises more than one wire, wherein the segment of each wire is positioned coaxially, and staggered relative to a segment of another wire, with respect to the longitudinal axis of the inspiratory conduit.

Optionally, each segment is deformed with respect to the longitudinal axis of the expiratory conduit. Optionally, the distal end of a first portion of a first segment of the wire and the proximal end of a second portion of an adjacent segment of the wire are spaced apart with respect to the longitudinal axis of the expiratory conduit. Optionally, the wire is formed from a series of at least two segments adjacently arranged with respect to the longitudinal axis of the expiratory conduit.

Optionally, the expiratory conduit comprises more than one resistor. Further optionally, the expiratory conduit comprises more than one wire. Optionally, the expiratory conduit comprises more than one wire, wherein each wire is positioned coaxially with respect to the longitudinal axis of the expiratory conduit. Optionally, the expiratory conduit comprises more than one wire, wherein each wire is positioned coaxially, and staggered relative to another wire, with respect to the longitudinal axis of the expiratory conduit. Optionally, the expiratory conduit comprises more than one wire, wherein the segment of each wire is positioned coaxially, and staggered relative to a segment of another wire, with respect to the longitudinal axis of the expiratory conduit.

Optionally, the humidified gas reservoir is a humidification chamber. Optionally, the humidification chamber has at least one inlet port and at least one outlet port. Optionally, in use the inlet port is in fluid communication with a gas supply, for example, in the case of a mechanical ventilator or other gas flow generating or receiving means. Optionally, in use, the outlet port is in fluid communication with the inspiratory conduit; optionally connected to the distal end of the inspiratory conduit. Optionally, at least part of the humidification chamber is sufficiently transparent to allow the passage of visible light therethrough. Optionally, the humidification chamber comprises a reservoir, which is adapted to receive and retain a fluid, optionally water, in an amount of about 10 to about 200 cm$^3$, optionally about 20 to about 180 cm$^3$, preferably about 100 to about 160 cm$^3$. Optionally or additionally, the reservoir is shaped and dimensioned to receive and retain fluid, optionally water; such that the fluid occupies a depth of the internal height of the reservoir of about 5 to about 50 mm.

Optionally, the method further comprises the step of regulating the relative humidity of the humidified gas from the humidified gas reservoir. Optionally, the humidification chamber comprises means to regulate the relative humidity of the gas therein. Optionally, the humidification chamber comprises means to regulate the amount of fluid, optionally water, received within the humidification chamber. Further optionally, the regulating means comprise a valve, optionally a buoyant valve. Still further optionally, the valve, optionally the buoyant valve, is adapted to cease water being received within the humidification chamber. Still further optionally, the buoyant valve comprises resilient, optionally a rubberised, surface; which, in use, forms a seal against the fluid, optionally water, being received within the humidification chamber.

Optionally, the humidification chamber has an internal cross sectional area of about 6,000 to about 10,000 mm$^2$. Further optionally, in use, about 7,000 to about 9,000 mm$^2$ of the cross-sectional area is occupied by a fluid, optionally water.

Optionally, the regulating means is adapted to allow the passage of water vapour therethrough. Optionally, in use, the regulating means is positioned on or at the surface of the fluid, optionally water, within the humidification chamber. Optionally, the regulating means is buoyant. Optionally, in use, the regulating means occludes about 30 to about 80% of the internal cross-sectional area of the humidification chamber. Optionally, in use, the regulating means occludes an area of the internal cross-sectional area of the humidification chamber of about 1,000 mm$^2$ to about 7,000 mm$^2$; optionally about 2,000 mm$^2$ to about 6,000 mm$^2$; preferably about 3,000 mm$^2$ to about 4,000 mm$^2$. Optionally, the regulating means is adapted to move reciprocally within the humidification chamber. Further optionally, the regulating means is adapted to move freely and reciprocally within the humidification chamber. Optionally, in use, the regulating means permits evaporation of water of about 30 to about 50 mg/L, optionally about 33 to about 46 mg/L, further optionally about 43 to about 45 mg/L, preferably about 44 mg/L; when the temperature of the humidified gas is about 37° C.

Optionally, the regulating means comprises at least one aperture, optionally such that at least part of the surface of the fluid, optionally water, within the humidification chamber is exposed to gas passing through the humidification chamber. Optionally, the regulating means is substantially planar in form and comprises at least one aperture.

By the term "planar" is meant the surface, optionally the in-use, gas-engagable face of the regulating means extends within a single, 2-dimensional plane. The regulating means can be substantially devoid of projections or protrusions, which extend from the surface, optionally the in-use, gas-engagable face of the regulating means.

Optionally, the regulating means is substantially planar in form and comprises six apertures. Optionally, at least one of the apertures is luniform in shape. Optionally, at least one of the apertures is crescent-shaped. Optionally or additionally, at least one of the apertures is circular in shape. Optionally or additionally, at least one of the apertures opens at an external edge of the regulating means. Optionally, the regulating means is generally penannular in shape. Optionally, the regulating means is substantially planar in form, generally penannular in shape, and comprises one luniform aperture, and four circular apertures.

Optionally, the regulating means is formed from an impermeable polymeric resin, optionally selected from amphorous and semi-crystalline polymers, optionally selected from polyolefins, polyamides, polyetheretherketones, and silicone. Alternatively, the regulating means is formed from a permeable material, such as open- or closed-cell polymeric foam or foamed polymer, optionally selected from foam or foamed amphorous and semi-crystalline polymers, optionally selected from foam or foamed polyolefins, foam or foamed polyamides, foam or foamed polyetheretherketones, and foam or foamed silicone. Optionally, the regulating means has a thickness of about 0.5 to about 5 mm, optionally about 1 to about 3 mm.

Optionally, the gas outlet is a mechanical ventilator.

BRIEF DESCRIPTION OF THE DRAWINGS

Embodiments of the present invention will now be described with reference to the accompanying drawings and examples in which.

DETAILED DESCRIPTION OF THE INVENTION

Figure 1:
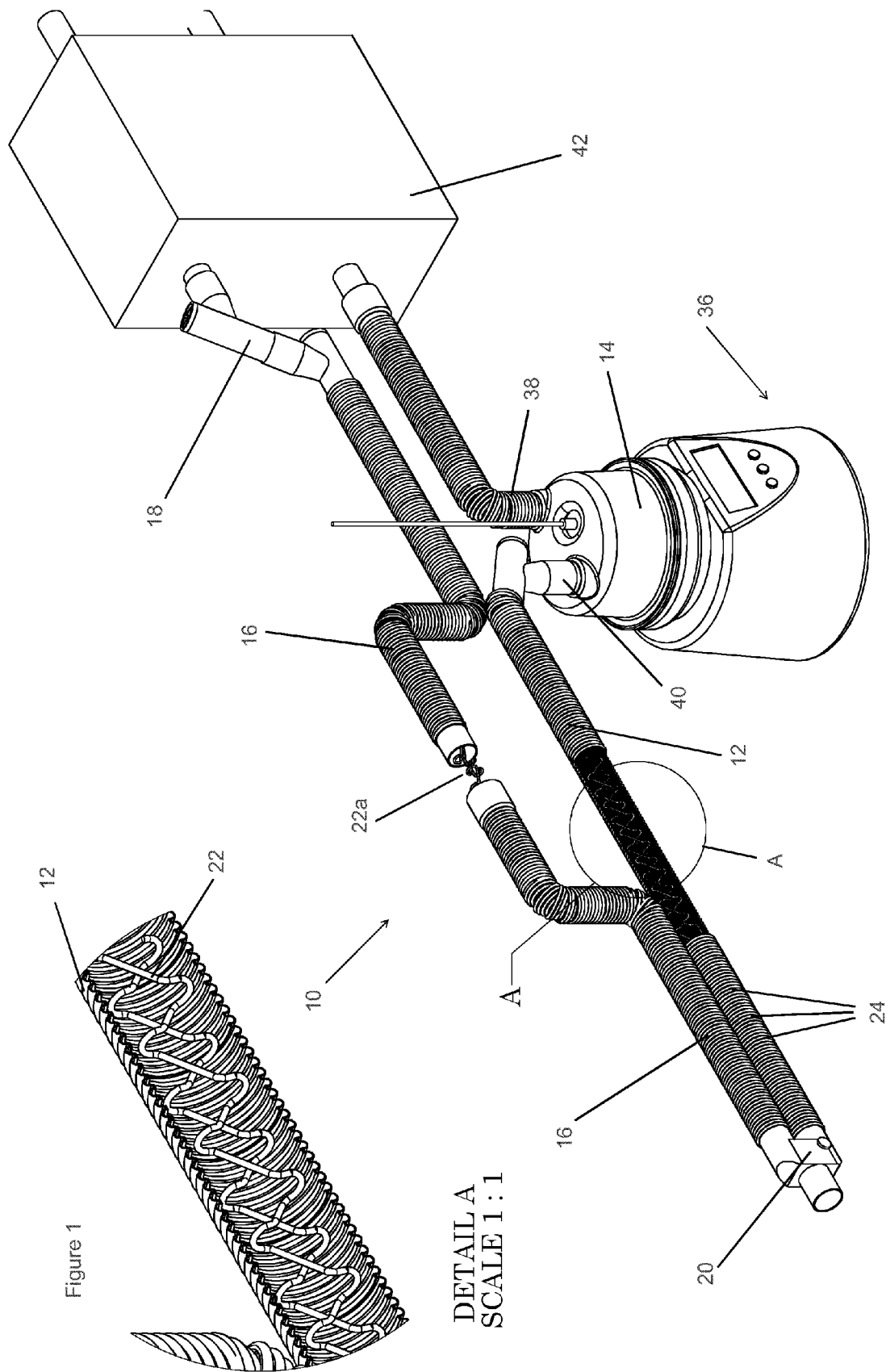
FIG. 1 is a perspective view of a humidified gas delivery system according to a first aspect of the present invention.

Referring now to FIG. 1, there is shown a perspective view of a humidified gas delivery system 10 according to a first aspect of the present invention. In a preferred embodiment, the humidified gas delivery system 10 comprises an inspiratory conduit 12 for transferring a humidified gas from a humidified gas reservoir 14 to a patient (not shown); means for heating the inspiratory conduit 12; an expiratory conduit 16 for transferring expired gas from a patient (not shown) to a gas outlet 18; and means for heating the expiratory conduit 16. The heating means are each arranged to heat the humidified gas and the expired gas to different temperatures.

The inspiratory conduit 12 can comprise a flexible pipe for transporting gases for inhalation from the humidified gas reservoir 14 to the patient. The expiratory conduit 16 can comprise a flexible pipe for transporting exhaled gases from the patient to the gas outlet 18.

A conduit connection 20 can be provided at or adjacent the proximal (relative to the patient) terminal end of each of the inspiratory 12 and expiratory 16 conduits. The conduit connection 20 is generally a Y-shaped connection and provided with a probe entry port (not shown) for measurement of gas temperature, which is, in use, in fluid communication with each of the inspiratory 12 and expiratory conduits 16. The conduit connection 20 can therefore deliver gases for inhalation from the humidified gas reservoir 14 to the patient via the inspiratory conduit 12, and receive exhaled gases from the patient to be transferred to the gas outlet 18. The conduit connection 20 can be in fluid communication with a delivery device, such as a facemask or nasal mask (not shown), wherein the delivery device is, in use, in fluid communication with the lungs of the patient. For example the delivery device can be a facemask, which is reversibly mountable to the face of the patient; or the delivery device can be a tracheal tube, which is located in the oral cavity or nasal orifice of the patient. In another embodiment, the delivery device can be mountable to a tracheostomy tube located in a tracheotomy stoma of the patient. Optionally, the conduit connection 20 and/or the delivery device are adapted to allow bi-directional and/or uni-directional passage of gas, such as the humidified gas from the humidified gas reservoir 14; such that the conduit connection 20 and/or the delivery device allows bi-directional and/or uni-directional passage of the humidified gas from the humidified gas reservoir 14 between the tracheo-bronchial bifurcation of the patient and each of the inspiratory 12 and/or expiratory 16 conduits of the humidified gas delivery system 10. In such an embodiment, the conduit connection 20, and each of the inspiratory 12 and expiratory 16 conduits together form a humidified gas delivery circuit, optionally a closed humidified gas delivery circuit, which transfers humidified gases from the humidified gas reservoir 14 for inhalation and humidified gases for exhalation to the gas outlet 18.

In a method of implementation, the expired gas in the expiratory conduit 16 is heated to a temperature from about 34° C. to about 44° C. In the method, the expired gas in the expiratory conduit 16 is heated to at least 38° C., optionally to at least 42° C., and preferably to about 44° C. It is understood that the expired gas in the expiratory conduit 16 can be heated to any suitable temperature, such that the expired gas is at about 44° C. at or adjacent the gas outlet 18. In a preferred embodiment, the expired gas in the expiratory conduit 16 is heated to sequentially along the length of the expiratory conduit 16, wherein the temperature is increased sequentially from about 34° C. to about 44° C. along the length of the expiratory conduit 16. For example, the expired gas can be heated to about 34° C. when received at or adjacent the patient, and is heated to a sequentially increasing temperature up to about 44° C. when received at or adjacent the gas outlet 18. It is understood that the expired gas is heated to a temperature such that the relative humidity of the expired gas is less than 90%, optionally less than 80%, further optionally less than 70%, still further optionally less than 60%, still further optionally less than 55%. The heated expired gas is transferred to the gas outlet 18 at less than about 55 mg/L, optionally less than 50 mg/L, preferably about 44 mg/L, in a preferred embodiment. The temperature of the external surface of the expiratory conduit 16; which is generally in contact with ambient conditions and under mechanical ventilation flow pattern of about 500 mL tidal volume at about 18 breaths per minute; is about 38° C. to about 44° C.; when the temperature is measured at a location at about 5% to about 10% of the total length of the expiratory conduit. In the case of an expiratory conduit 16 having a total length of 1 m, the temperature of the expired gas is preferably about 38° C. to about 44° C. at a location between about 5 and about 10 cm from the gas outlet 18.

In a preferable embodiment, the heated humidified gas is transferred from the humidified gas reservoir 14 to the patient at about 30 to about 50 mg/L, optionally about 33 to about 46 mg/L, preferably about 43 to about 45 mg/L, more preferably 44 mg/L. The humidified gas from the humidified gas reservoir 14 is heated to a temperature from about 28° C. to about 40° C. In a preferred embodiment, the humidified gas in the inspiratory conduit 12 is heated to about 32° C., optionally to about 36° C., and preferably to about 37° C. The humidified gas in the inspiratory conduit 12 is preferably heated to about 37° C. at or adjacent the gas reservoir 14. Optionally, the humidified gas in the inspiratory conduit 12 is heated to a sequentially increasing temperature from about 28° C. to about 40° C. along the length of the inspiratory conduit 12. For example, the humidified gas can be heated to about 37° C. when received at or adjacent the gas reservoir 14, and can be heated to about 40° C. when received at or adjacent the patient. In a preferred method, the humidified gas in the inspiratory conduit 12 is heated to about 37° C. when received at or adjacent the gas reservoir 14, and is heated to a sequentially increasing temperature along the length of the inspiratory conduit 12 up to about 40° C. when received at or adjacent the patient. In a preferred embodiment, the humidified gas in the inspiratory conduit 12 can be heated to a temperature such that the relative humidity of the humidified gas from the humidified gas reservoir is at least 50%, optionally at least 60%, further optionally at least 70%, still further optionally at least 80%, still further optionally at least 90%. It is understood that the temperature of the external surface of the inspiratory conduit 12; which is generally in contact with ambient conditions and under mechanical ventilation flow pattern of about 500 mL tidal volume at about 18 breaths per minute; is about 33° C. to about 40° C., when the temperature is measured at a location at about 5% to about 10% of the total length of the inspiratory conduit 12. In the case of an inspiratory conduit 12 having a total length of 1 m, the temperature of the humidified gas is preferably about 33° C. to about 38° C. at a location between about 5 and about 10 cm from the humidified gas reservoir 14.

In a preferred embodiment, the humidified gas in the inspiratory conduit 12, and the expired gas in the expiratory conduit 16, is heated using an electrically conductive resistor 22, 22a. The resistor 22, 22a can be formed from a material having a resistivity of about $0.1 \times 10^{-3}$ Ωm to about $25.0 \times 10^{-3}$ Ωm at about 20° C., and preferably such that the power dissipated by the resistor 22, 22a is from about 18 to about 42 watts. The humidified gas in the inspiratory conduit 12 is heated using an electrically conductive resistor 22, wherein the power dissipated by the resistor 22 is from about 18 to about 34 watts, optionally from about 20 to about 30 watts, further optionally from about 22 to about 28 watts; and the expired gas in the expiratory conduit 16 is heated using an electrically conductive resistor 22a, wherein the power dissipated by the resistor 22a is from about 28 to about 42 watts, optionally from about 30 to about 40 watts, further optionally from about 32 to about 38 watts.

The resistor 22, 22a can have an electrical resistance of no more than 25 ohms about 20° C. The humidified gas in the inspiratory conduit 12 can be heated using an electrically conductive resistor 22 having an electrical resistance of about 16 ohms at about 20° C.; and the expired gas in the expiratory conduit 16 can be heated using an electrically conductive resistor 22a having an electrical resistance of about 12 ohms at about 20° C.

Current can be supplied to the resistor 22, 22a in a continuous or semi-continuous manner. In a preferred embodiment, current is supplied to the resistor 22 when the humidified gas is below a first temperature. In a preferred embodiment, current is supplied to the resistor 22 when the humidified gas is below a first temperature; and current is not supplied to the resistor when the humidified gas is above a second temperature 22; wherein the first and second temperatures are the same or different temperatures. Similarly, current can be supplied to the resistor 22a when the expired gas is below a first temperature; and current is not supplied to the resistor 22a when the expired gas is above a second temperature; wherein the first and second temperatures are the same or different temperatures.

The humidified gas in the inspiratory conduit 12 is heated using an electrically conductive resistor 22, wherein current is supplied to the resistor 22 when the humidified gas is below a first temperature of about 28° C., preferably about 37° C. The humidified gas in the inspiratory conduit 12 is heated using an electrically conductive resistor 22, wherein current is not supplied to the resistor 22 when the humidified gas is above a second temperature of about 40° C., preferably about 44° C. Optionally or additionally, the humidified gas in the inspiratory conduit 12 is heated using an electrically conductive resistor 22, wherein current is not supplied to the resistor 22 when the difference in the temperature of the humidified gas when measured at or adjacent the humidified gas reservoir 14, and the temperature of the humidified gas when measured at or adjacent the patient, is more than 3° C.

The expired gas in the expiratory conduit 16 is heated using an electrically conductive resistor 22a, wherein current is supplied to the resistor 22a when current is supplied to the resistor 22 in the inspiratory conduit 12.

The resistor, such as a wire 22, 22a can be capable of carrying alternating current, for example from a mains supply of current; or direct current, for example from a battery or cell. In a preferred embodiment, the wire 22, 22a is capable of carrying alternating current or direct current up to 3 amperes. The wire 22, 22a is at least partially surrounded by an electrically non-conductive polymeric material, such as polyolefins and polyamides, for example polypropylene or nylon, although the skilled person can readily select any suitable electrically non-conductive polymeric material. The thickness of the electrically non-conductive polymeric material is about 0.2 to about 2 mm, preferably about 0.4 to about 1 mm. The resistor, such as the wire 22, 22a, can be formed from a metal or an alloy; although one skilled in the art may select any suitable material having the required resistivity. In a preferred embodiment, the resistor 22, 22a, such as the wire 22, 22a, is formed from a metal or an alloy selected from Aluminum; Brass; Carbon, optionally amorphous Carbon; Constantan; Copper; Iron; Manganin; Molybdenum; Nichrome; Nickel; Platinum; Stainless steel; Steel; Tungsten; and Zinc.

The inspiratory conduit 12 is arranged to allow the passage of the heated humidified gas therethrough and, in a preferred embodiment, the inspiratory conduit 12 comprises a hollow cylindrical tube having open ends. In a preferred embodiment, the internal diameter of the inspiratory conduit 12 is about 10 to about 32 mm, preferably about 20 to about 22 mm. The inspiratory conduit 12 can comprise circumferential recesses 24, optionally a plurality of repeated circumferential recesses, along at least a portion of the inspiratory conduit 12. The circumferential recesses 24 can extend along at least a portion of the inner surface of the inspiratory conduit 12. The inspiratory conduit 12 can be arranged to receive a resistor 22 within the lumen thereof. In a preferred embodiment, the inspiratory conduit 12 further comprises means to secure the resistor 22 within the lumen thereof. In a particularly preferred embodiment, the resistor 22 is a wire having a generally constant cross-sectional dimension. The wire 22 can have a resistance of about 1.5 to about 3.0 ohms, preferably 2.0 ohms, per meter length.

Figure 2:
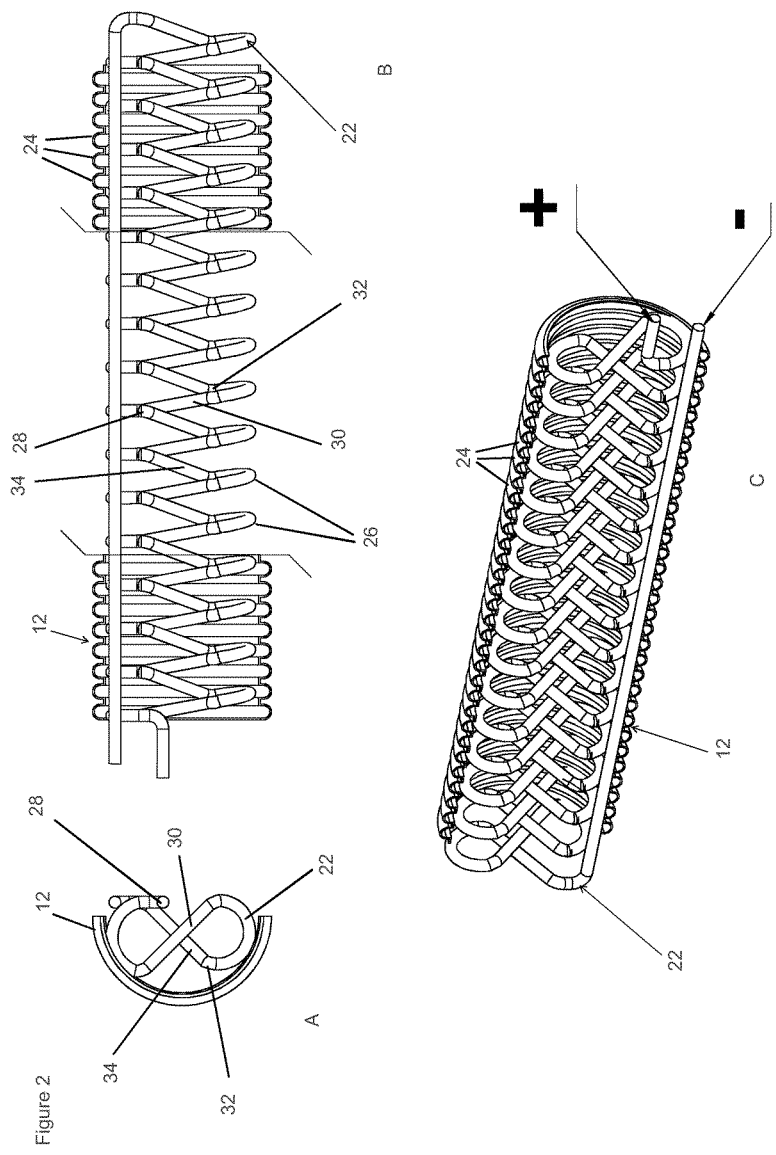
FIG. 2A is a transverse cross-sectional view of an inspiratory conduit according to a first embodiment of a second aspect of the present invention.
FIG. 2B is a longitudinal cross-sectional view of the inspiratory conduit of FIG. 2A.
FIG. 2C is a perspective view of the inspiratory conduit of FIG. 2B.

Referring to FIG. 2, there is shown a transverse cross-sectional view (2A); a longitudinal cross-sectional view (2B); and a perspective view (2C) of an inspiratory conduit 12 according to a first embodiment of the present invention. In use, the resistor 22, for example the wire 22, can be positioned within the lumen of the inspiratory conduit 12. At least part of the wire 22 can be arranged to extend circumferentially within at least a portion of the lumen of the inspiratory conduit 12; and at least part of the wire 22 can be arranged to extend diametrically across the lumen of the inspiratory conduit 12. In a preferred embodiment, the wire 22 is formed from a series of at least two segments 26, wherein each segment 26, at least part of the wire 22 is arranged to extend circumferentially within at least a portion of the lumen and at least part of the wire is arranged to extend diametrically across the lumen of the inspiratory conduit 12.

Similarly, in use, the resistor 22a, optionally the wire 22a, is positioned within the lumen of the expiratory conduit 16; wherein at least part of the wire 22a is arranged to extend circumferentially within at least a portion of the lumen of the expiratory conduit 16; and at least part of the wire 22a is arranged to extend diametrically across the lumen of the expiratory conduit 16. The wire 22a can be formed from a series of at least two segments 26, wherein each segment 26, at least part of the wire 22a is arranged to extend circumferentially within at least a portion of the lumen and at least part of the wire 22a is arranged to extend diametrically across the lumen of the expiratory conduit 16.

For ease of reference, the wire 22 positioned within the lumen of the inspiratory conduit 12, will be generally described with reference to FIG. 2; although the description is also with reference to the wire 22a positioned within the lumen of the expiratory conduit 16, which has similar features. In a preferred embodiment, each segment 26 has a serpentine form, for example each segment 26 is shaped in the form of the letter "S"; and has a first end 28, a middle portion 30, a second end 32, and a connector 34. The portion of the wire segment adjacent the first end 28 is substantially curvilinear in form; the portion of the wire segment adjacent the middle portion 30 is substantially linear in form; the portion of the wire segment adjacent the second end 32 is substantially curvilinear in form; and the portion of the wire adjacent the connector 34 is substantially linear in form. In a preferred embodiment, the portion of the wire segment adjacent the first end 28 is substantially curvilinear in form, the portion of the wire segment adjacent the second end 32 is substantially curvilinear in form; and each is connected by a portion of the wire segment adjacent the middle portion 30, which is substantially linear in form. The portion of the wire adjacent the connector 34 is substantially linear in form and extends between the second end 32 of a first segment 26 of the wire and the first end 28 of an adjacent segment 26 of the wire. The connector 34 can be generally oriented in opposing direction to the middle portion 30 of each segment 26, as is generally illustrated in FIG. 2A.

As can be seen in FIGS. 2B and 2C, each segment 26 is deformed with respect to the longitudinal axis of the inspiratory conduit 12, such that the first end 28 and the second end 32 of each segment 26 are spaced apart with respect to the longitudinal axis of the inspiratory conduit 12. In a preferred embodiment, the wire 22 is formed from a series of at least two segments 26 adjacently arranged with respect to the longitudinal axis of the inspiratory conduit 12.

Figure 3:
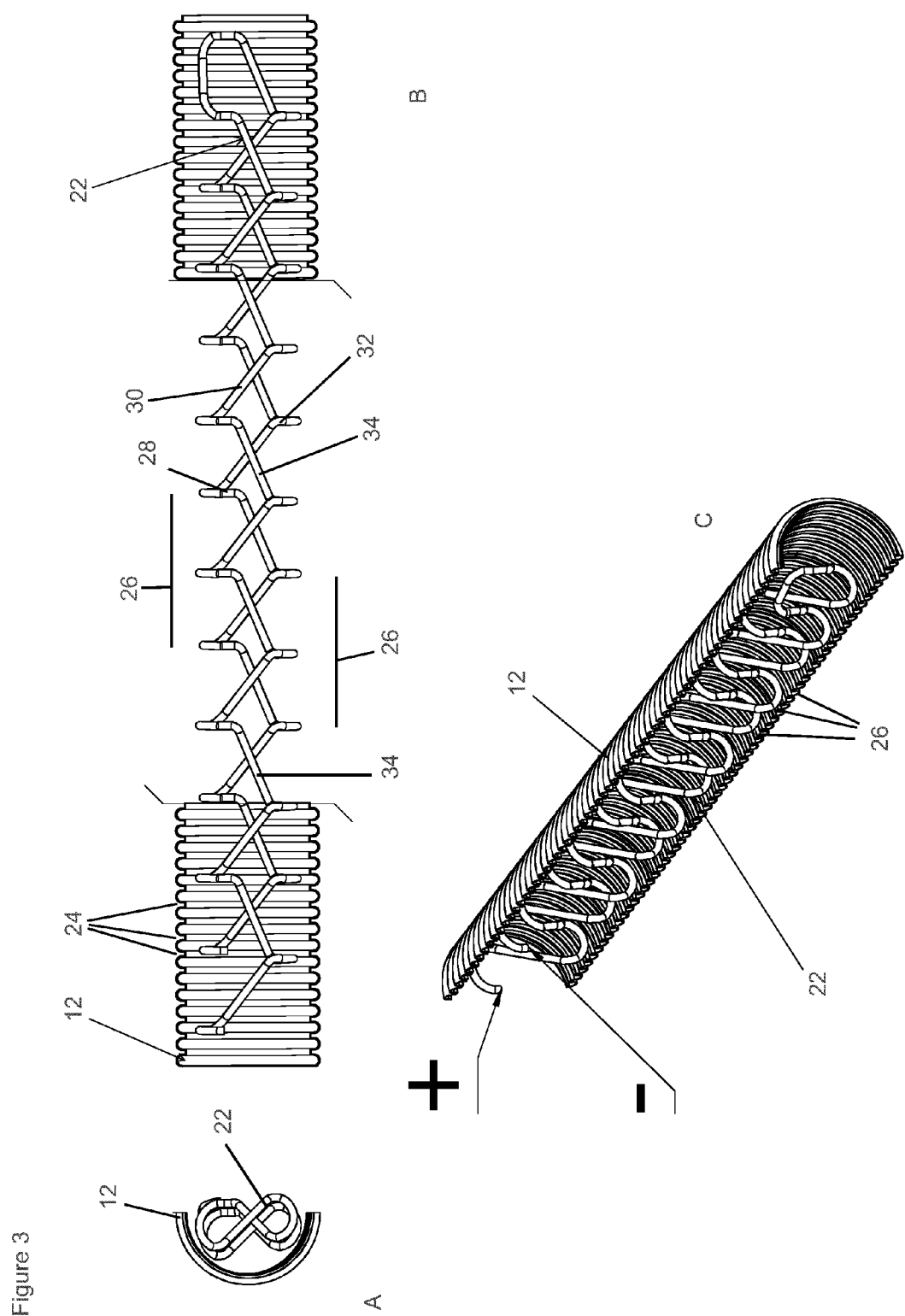
FIG. 3A is a transverse cross-sectional view of an inspiratory conduit according to a second embodiment of the second aspect of the present invention.
FIG. 3B is a longitudinal cross-sectional view of the inspiratory conduit of FIG. 3A.
FIG. 3C is a perspective view of the inspiratory conduit of FIG. 3B.
Figure 4:
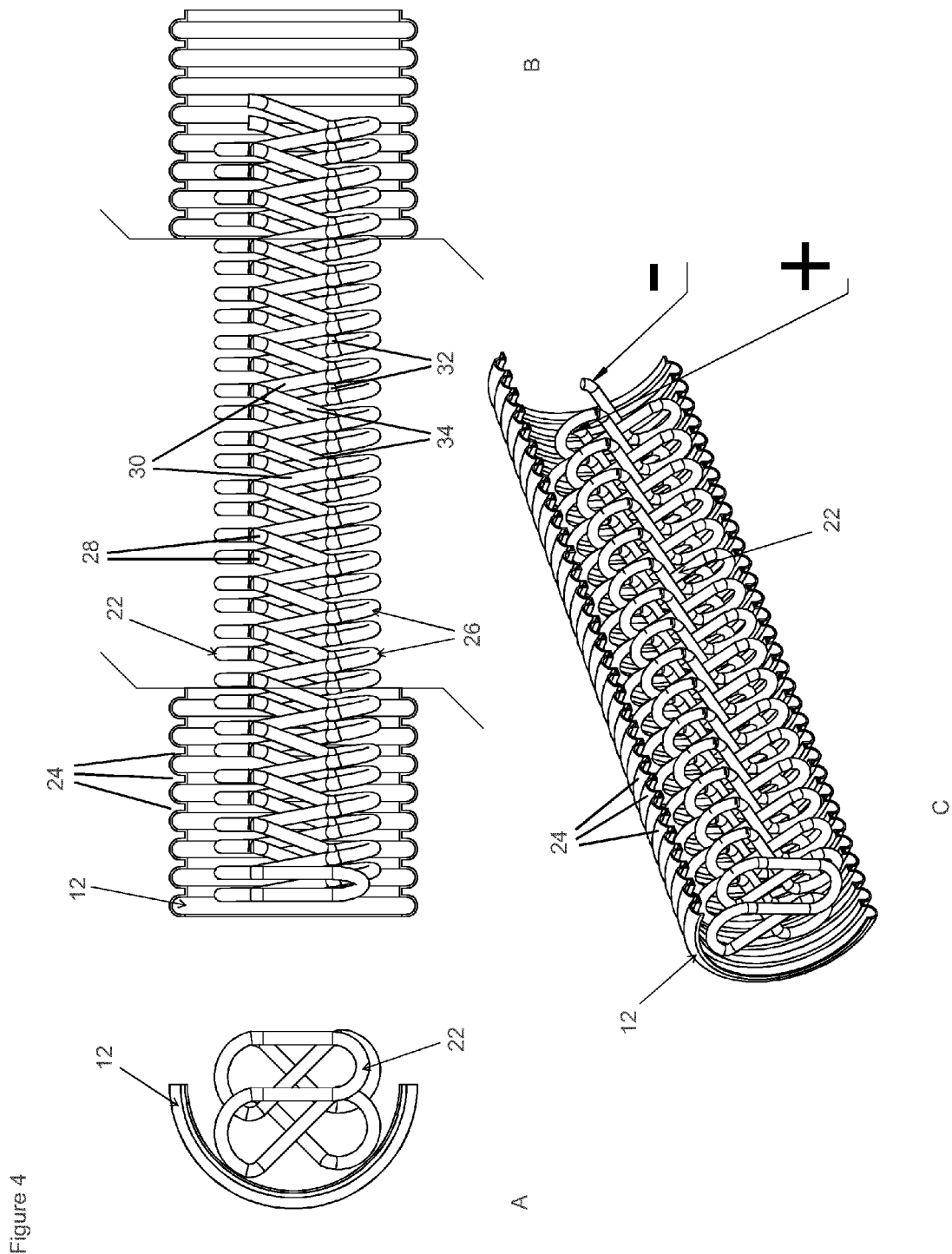
FIG. 4A is a transverse cross-sectional view of an inspiratory conduit according to a third embodiment of the second aspect of the present invention.
FIG. 4B is a longitudinal cross-sectional view of the inspiratory conduit of FIG. 4A.
FIG. 4C is a perspective view of the inspiratory conduit of FIG. 4B.

In an alternative embodiment, as illustrated in FIGS. 3 and 4, the inspiratory conduit 12 comprises more than one resistor 22, such as a wire 22. The inspiratory conduit 12 can comprise more than one wire 22, wherein each wire 22 is positioned coaxially with respect to the longitudinal axis of the inspiratory conduit 12, as is illustrated in FIG. 3. The inspiratory conduit 12 can comprise more than one wire 22, wherein each wire 22 is positioned coaxially, and staggered relative to another wire 22, with respect to the longitudinal axis of the inspiratory conduit 12.

In a further alternative embodiment, as illustrated in FIG. 4, the inspiratory conduit 12 can comprise more than one resistor 22, such as a wire 22; wherein each wire 22 is positioned adjacent or in side-by-side relationship with respect to the another wire 22, and staggered relative to the other wire 22 with respect to the longitudinal axis of the inspiratory conduit 12.

Figure 5:
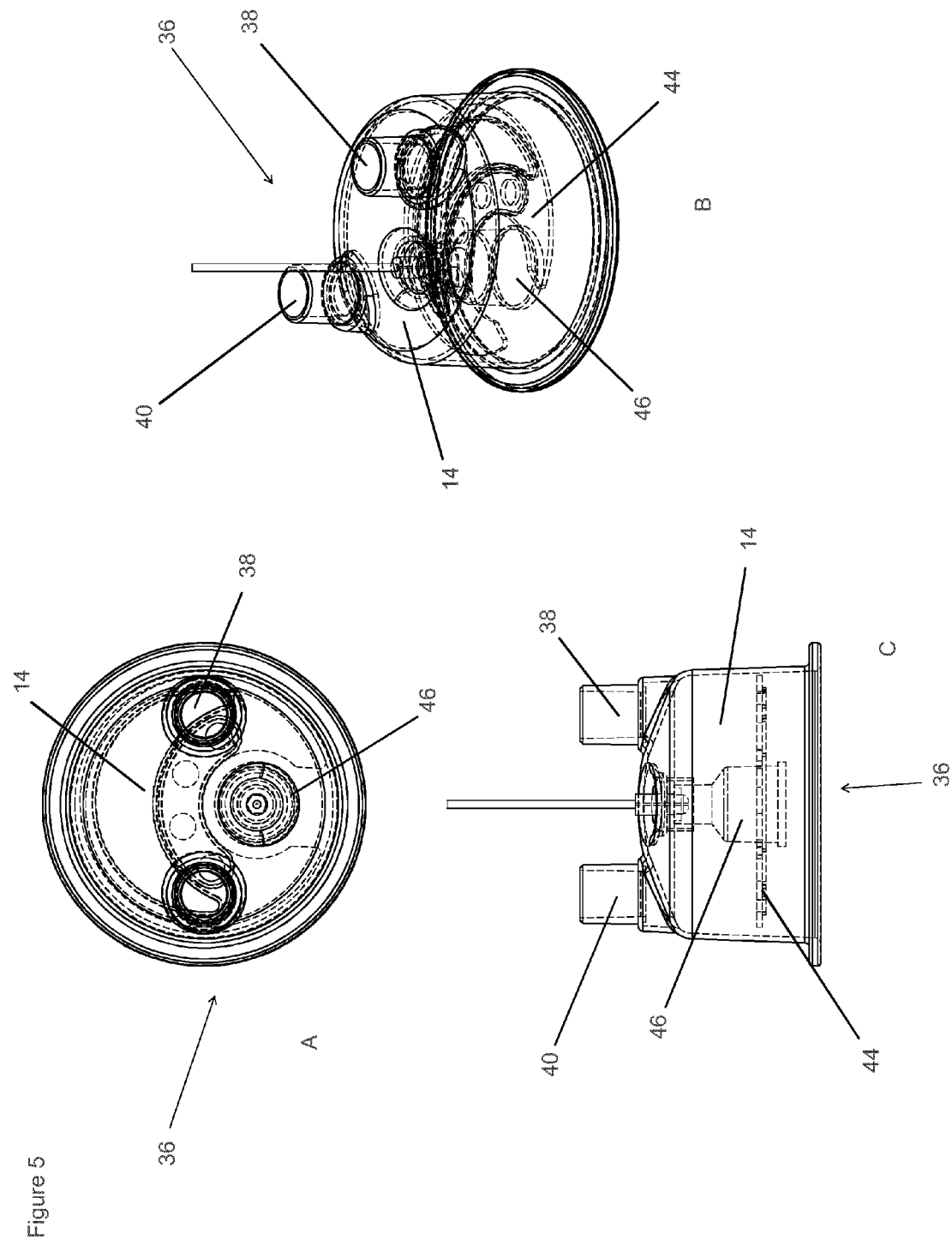
FIG. 5A is a plan sectional view of a humidification chamber of the humidified gas delivery system of FIG. 1.
FIG. 5B is a perspective sectional view of the humidification chamber of FIG. 5A.
FIG. 5C is a side sectional view of the humidification chamber of FIG. 5A.

Referring now to FIG. 5, there is shown a plan sectional view (5A); is a perspective sectional view (5B); and a side sectional view (5C) of a humidification chamber 36 of the humidified gas delivery system 10. The humidification chamber 36 comprises the humidified gas reservoir 14, and at least one inlet port 38 and at least one outlet port 40 provided with a probe entry port (not shown) for measurement of gas temperature. Generally, the inlet port receives a fluid, such as a gas, from a gas source, such as a mechanical ventilator 42 (see FIG. 1) and transfers the gas to humidified gas reservoir 14. The gas from the gas source, such as the mechanical ventilator 42, is humidified in the humidified gas reservoir 14, and the humidified gas is transferred to the inspiratory conduit 12 via the outlet port 40. At least part of the humidification chamber 36 can be sufficiently transparent to allow the passage of visible light therethrough. The humidified gas reservoir 14 is adapted to receive and retain a fluid, optionally water, in an amount of about 10 to about 200 $cm^3$, optionally about 20 to about 180 $cm^3$, preferably about 100 to about 160 $cm^3$; and is generally shaped and dimensioned to receive and retain the fluid, optionally water; such that the fluid occupies a depth of the internal height of the reservoir of about 5 to about 50 mm; although the shape and dimension can be selected by one skilled in the art.

Optionally, the humidification chamber comprises means to regulate the amount of fluid, optionally water, received 46 within the humidification chamber 36. The fluid regulating means 46 can comprise a valve, optionally a buoyant valve. The valve 46, optionally the buoyant valve 46, is adapted to cease water being received within the humidification chamber 36; and can comprise a resilient, optionally a rubberised, surface; which can form a seal against the fluid, optionally water, being received within the humidification chamber 36.

The humidification chamber 36, specifically, the humidified gas reservoir 14 generally has an internal cross sectional area of about 6,000 to about 10,000 $mm^2$. In use, about 7,000 to about 9,000 $mm^2$ of the cross-sectional area is occupied by a fluid, optionally water.

Figure 6:
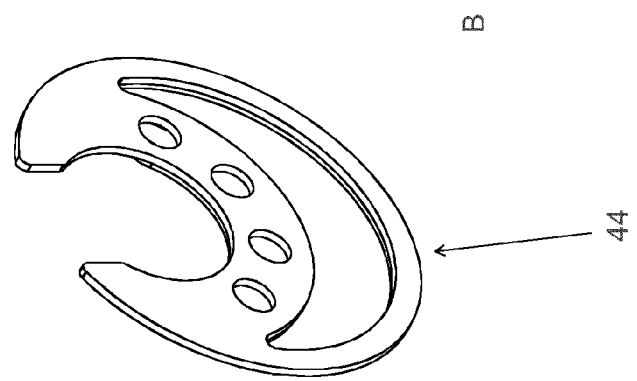
FIG. 6A is a plan view of regulating means of the humidification chamber of FIG. 5A.
FIG. 6B is a perspective view of the regulating means of FIG. 6A.
Figure 6:
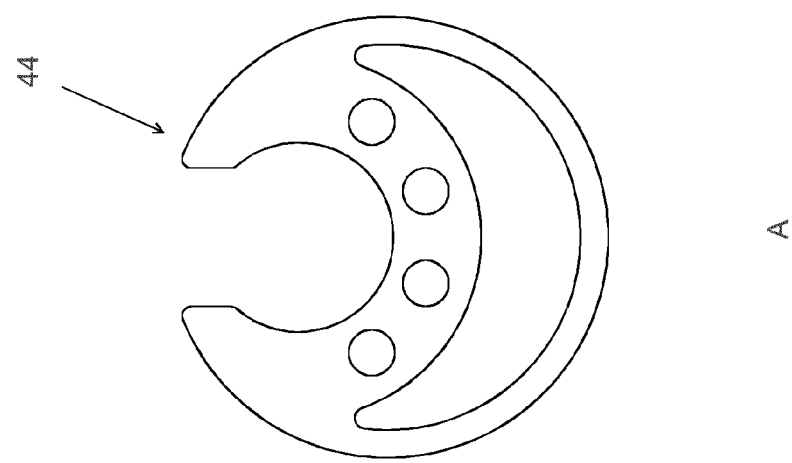

In a preferred embodiment, the method of the present invention further comprises the step of regulating the relative humidity of the humidified gas. The humidification chamber 36 can comprise means to regulate the relative humidity 44 of the gas therein. FIG. 6A is a plan view of regulating means 44 of the humidification chamber 38. The regulating means 44 is adapted to allow the passage of water vapour therethrough; and, in use, the regulating means 44 is positioned on or at the surface of the fluid, optionally water, within the humidification chamber 38; specifically on or at the surface of the fluid, optionally water, within the humidified gas reservoir 14 of the humidification chamber 38. In a preferred embodiment, the regulating means is buoyant; and, in use, the regulating means 44 occludes about 30 to about 80% of the internal cross-sectional area of the surface of the fluid, optionally water, within the humidified gas reservoir 14 of the humidification chamber 38. In use, the regulating means 44 occludes an area of the internal cross-sectional area of the surface of the fluid, optionally water, within the humidified gas reservoir 14 of the humidification chamber 38 of about 1,000 mm$^2$ to about 7,000 mm$^2$; preferably about 3,000 mm$^2$ to about 4,000 mm$^2$. The regulating means 44 is adapted to move freely and reciprocally within the humidification chamber 38, and with the changing level of the fluid, such as water, within the humidified gas reservoir 14. The regulating means 44 preferably comprises at least one aperture, such that at least part of the surface of the fluid, such as water, within the humidification chamber 38 is exposed to gas passing through the humidification chamber 38. In a particularly preferred embodiment, the regulating means 44 is substantially planar in form and comprises six apertures. At least one of the apertures is luniform in shape (crescent-shaped); at least one of the apertures opens at an external edge of the regulating means 44, such that the regulating means 44 is generally penannular in shape; and four of the apertures are circular apertures. The regulating means 44 can be formed from an impermeable polymeric resin, such as amphorous and semi-crystalline polymers, for example polyolefins, polyamides, polyetheretherketones, and silicone. Alternatively, the regulating means can be formed from a permeable material, such as open- or closed-cell polymeric foam or foamed polymer. The regulating means 44 preferably has a thickness of about 0.5 to about 5 mm, optionally about 1 to about 3 mm.

Advantageously, in the present invention, the humidified gas delivery system 10 comprises a control system, which discriminates between which temperatures are reached adjacent the humidified gas reservoir 14 and adjacent the conduit connection 20 by regulating the temperature of the humidified gas, and regulating the relative humidity of the humidified gas, in view of the levels of humidified gas required by the patient. For example, a patient whose trachea is intubated using an oral or nasal tracheal tube or tracheostomy tube may require gases for inhalation that are at a temperature which is based on achieving inhaled humidified gas temperature of 37° C. at the conduit connection 20. Conversely, a patient which is not intubated but is, instead, fitted with a face mask may require gases for inhalation that are at a temperature which is based on achieving inhaled humidified gas temperature of 34° C. at the patient connection. Discrimination between which gas temperatures are reached is an operator decision, ordinarily based on how much of the patient's natural airway passages are bypassed or somehow otherwise restricted as necessitated by the equipment used in providing a secure airway path into and from the patient's lungs to conduct respiratory gas ventilation support.

Without being bound by theory, it is thought that disturbance to the surface of the water in the humidified gas reservoir 14 of the humidification chamber 38 by gas flowing through the humidified gas reservoir 14 is cause for an increase in the total surface area of the water in the humidified gas reservoir 14. Such an increase in surface area is effected by the volume and/or velocities of gas flowing through the humidified gas reservoir 14. In physical appearance, such disturbance to the otherwise planar surface of the water is that of 'waves'. Generally, as gas volume and/or velocities of gas flow increases through the humidified gas reservoir 14, the total surface area of water exposed to such gas flow is increased; which can lead to water vapour production in excess of that capable of remaining as water vapour in gas of a chosen temperature. Such events inevitably result in unintentional condensing of this excess water vapour. Whilst clinical therapeutic requirements require a wide range of gas flow volume and gas flow velocities, they do not require such gases to be laden with water vapour in excess of the maximum that can be carried in the gases at a chosen gas temperature.

It is also thought that unintentional changes to compressible volume of the 'free space' in the humidified gas reservoir 14 causes disturbance to the surface of the water. By 'free space' is meant the volume of the humidified gas reservoir 14 not occupied by water. A method by which to maintain consistent volume of 'free space' in the humidified gas reservoir 14 is preferable, but is not taught in prior art. A factor contributing to unintentional accumulation of condensed water in the prior art is inconsistent evaporation of water in the humidified gas reservoir 14; the inconsistencies arising when certain of the gas flow velocities pass through the humidified gas reservoir 14. A method by which to avoid unnecessary production of water vapour is preferable, but is neither disclosed, nor taught in the prior art. Further, a method by which to produce water vapour at a consistent level without dependence on using particular gas flow volume and/or gas flow velocities is preferable, but is not disclosed in the prior art.

Accordingly, the present invention selectively regulates the relative humidity of the humidified gas in the humidified gas, and selectively regulates the temperature of the humidified gas and the expired gas to try to ensure that condensation of the water vapour from the humidified gas or the expired gas does not occur within the humidified gas delivery system 10.

EXAMPLES

Example 1

A direct comparative test was undertaken under the following conditions: Humidification chambers of a humidified gas delivery system according to the present invention and a humidified gas delivery system of the prior art comprising a Fisher Paykel model MR290 humidification chamber (Fisher Paykel Healthcare, Auckland, New Zealand) were compared in a direct comparative test. Both humidified gas delivery systems were tested using a Maquet Servo 300 ventilator (Maquet Ltd., Sunderland, UK) as ventilation source and heater humidifier model MR850 (Fisher Paykel Healthcare, Auckland, New Zealand) in 'tracheal mode' as heater base; and the following settings and conditions were identical in both systems:
Tidal volume: 500 mL at 21% oxygen;
Respiratory rate: 18 breaths per minute;
Ventilation ratio: I:E 1:2;

PEEP: 5 cmH$_2$O;
Ambient temperature: 21° C. at 30-50% humidity; and
Ambient air speed: <5 cm·s at 1 atmosphere.

Both systems were arranged generally in accordance with FIG. 1 (or according to the manufacturer's instructions), and allowed to run for a stabilisation time of approximately 3-hours, before the start of the test. Data were recorded at 16-hours after start. Each system was attached to a Maquet 1.0 L patient lung, maintained at 37° C.; and temperatures were measured using a DM509-TX-01 Temperature measurement instrument (Rense Instruments, Oosterhout, NL). A water-containing vessel was primed with de-ionised water with an amount that exceeded the amount required to fill the humidification chamber to its 'auto-fill' level and thought necessary to supply the humidification chamber with water for evaporation for >16 hours. The water-containing vessel, when connected to a feed line connected to the humidification chamber, released water to the humidification chamber until the water fill valving mechanism of the humidification chamber was actuated to cease flow of water to the humidification chamber. The water contained in the humidification chamber was deemed the 'auto-fill' quantity. The water-containing vessel was then valved-off and disconnected from the system prior to being weighed to establish the net weight of remaining water in the water-containing vessel. Weight was calculated using a weight measurement instrument (Adam Equipment, Danbury, USA). Measurements were taken in triplicate and the average net weight of water calculated. The water-containing vessel was then reconnected to the water feed line of the humidification chamber and the valved set to open. This provided an open circuit for water to refill the humidification chamber to replace water evaporated by gas flow and heat. The test then started. At 16-hours, the water-containing vessel was again valved-off and disconnected from the system prior to being weighed to establish the net weight of remaining water in the water-containing vessel. Weight was calculated using the weight measurement instrument. Measurements were taken in triplicate and the average net weight of water calculated. The difference in weights of water between the start and at 16-hours was quantified in milligrams then divided by the total gas flow passing through the humidification chamber in 16-hours to quantify the milligrams of water evaporated per liter of gas flow flowing through the humidification chamber during 16 hours.

| Ventilation Parameters (I:E 1:2) | Prior Art | Present Invention |
|---|---|---|
| Tv700 mL/12RR | 39.6 | 43 |
| Tv650 mL/15RR | 41.8 | 43.1 |
| Tv600 mL/18RR | 43.8 | 43.2 |
| Tv550 mL/21RR | 44.2 | 43.4 |
| Tv500 mL/24RR | 44.9 | 43.6 |
| Tv450 mL/27RR | 43.6 | 43.1 |
| Tv400 mL/30RR | 44.1 | 43.2 |
| Tv350 mL/33RR | 45.8 | 43.8 |

Figure 7:
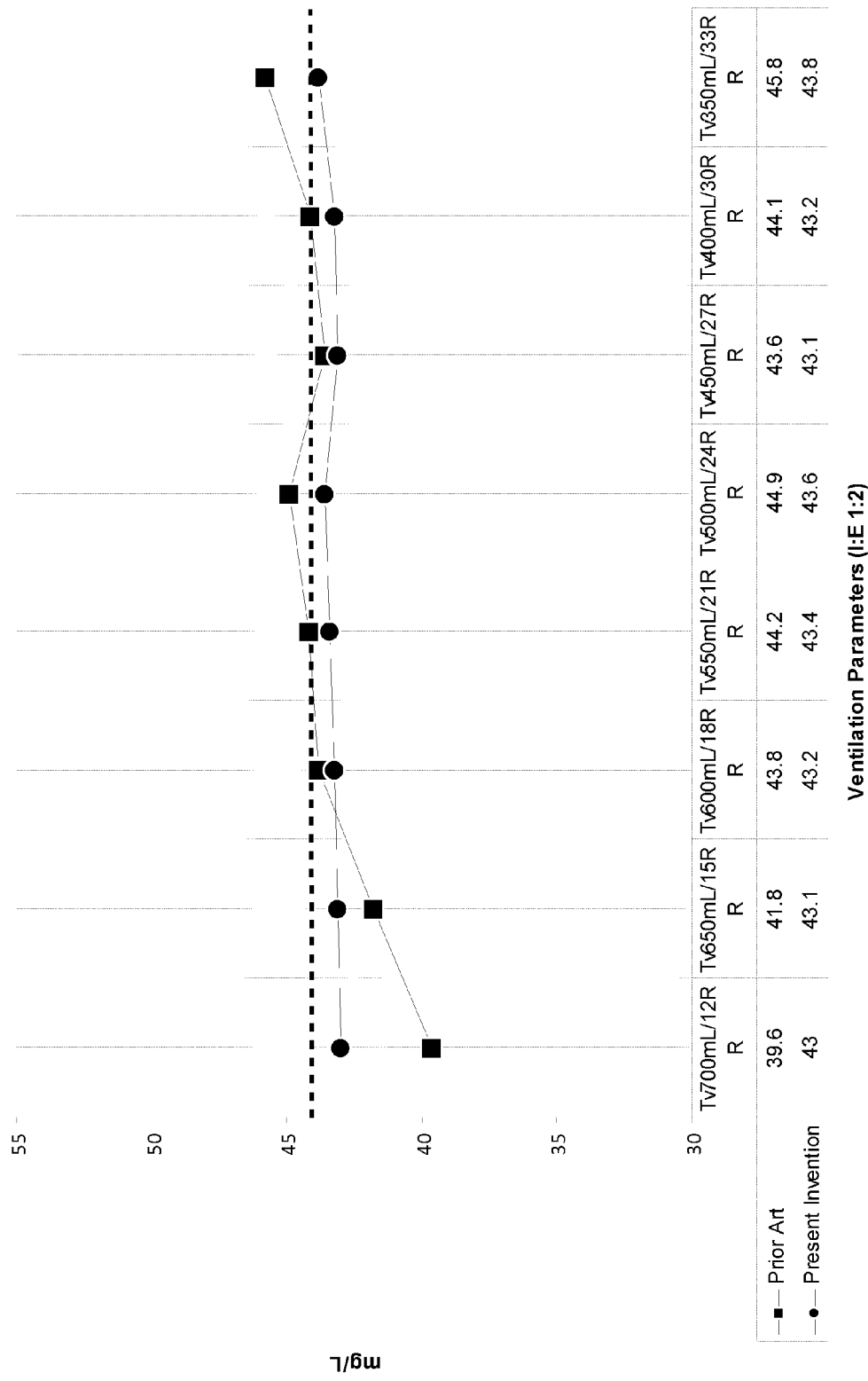
FIG. 7 is a graph illustrating a direct comparative test between a humidified gas delivery system according to the present invention and a humidified gas delivery system of the prior art.

The results are plotted in FIG. 7. The dashed line indicates 100% RH at 37° C. is 44 mg/L flow. The data demonstrate that the humidification chamber of the present invention produces a level of humidity consistently closer to 44 mg/H$_2$O and below 44 mg/H$_2$O than does the humidification chamber of the prior art.

Example 2

A direct comparative test was undertaken under the following conditions: A humidified gas delivery system according to the present invention and humidified gas delivery systems of the prior art comprising Fisher Paykel model RT200 (Fisher Paykel Healthcare, Auckland, New Zealand) (prior art 1) and Intersurgical model 2026310 (Intersurgical (UK) Limited, Wokingham, UK) (prior art 2) The humidified gas delivery systems were tested using a Maquet Servo 300 ventilator (Maquet Ltd., Sunderland, UK) as ventilation source and heater humidifier model MR850 (Fisher Paykel Healthcare, Auckland, New Zealand) in 'tracheal mode' as heater base and wherein an intervention was made to alter the target temperatures of humidified gas at the outlet port of the humidification chamber (for example, see 40 of FIG. 1) to suit the range of inlet conduit temperatures required for the tests. The following settings and conditions were identical in the systems:
Tidal volume: 500 mL at 21% oxygen;
Respiratory rate: 18 breaths per minute;
Ventilation ratio: I:E 1:2;
PEEP: 5 cmH$_2$O;
Ambient temperature: 21° C. at 30-50% humidity; and
Ambient air speed: <5 cm·s at 1 atmosphere.

The systems were arranged generally in accordance with FIG. 1 (or according to the manufacturer's instructions), and allowed to run for a stabilisation time of approximately 3-hours before the start of the test. Data were recorded at 16-hours after start. Each system was attached to a Maquet 1.0 L patient lung, maintained at 37° C.; and temperatures were measured using a DM509-TX-01 Temperature measurement instrument (Rense Instruments, Oosterhout, NL). A supply of de-ionised water was made available to fill the humidification chamber to maintain its 'auto-fill' level and was sufficient to supply the humidification chamber with water for evaporation for >16 hours. The relevant conduit sub-assemblies of the systems were weighed before the start of the test using an ACB 150 weight measurement instrument (Adam Equipment, Danbury, USA). Measurements were taken in triplicate and the average net weight calculated. The conduits were again weighed at 16-hours after start, in order to establish a difference in weight between the start of the test and the 16-hours caused by accumulation of condensed water along any part of the conduit sub-assembly. Measurements were taken in triplicate and the average net weight gain calculated.

| | Conduit inlet T (° C.) | *Conduit outlet T (° C.) | Present Invention ** rain-out (mgH$_2$O) | Prior art 1 ** rain-out (mgH$_2$O) | Prior art 2 ** rain-out (mgH$_2$O) |
|---|---|---|---|---|---|
| Inspiratory conduit | 30 | 32 | 2,990 | 6,350 | 16,500 |
| | 30 | 34 | 2,355 | 6,900 | 17,600 |
| | 32 | 34 | 3,050 | 7,840 | 17,000 |
| | 32 | 36 | 2,350 | 7,320 | 17,000 |
| | 35 | 37 | 3,400 | 8,150 | 17,500 |
| | 35 | 39 | 2,400 | 7,950 | 16,500 |
| | 37 | 39 | 3,670 | 7,900 | 19,600 |
| | 37 | 41 | 2,650 | 7,700 | 18,200 |
| | 39 | 41 | 3,980 | 7,850 | 19,500 |
| | 39 | 43 | 3,150 | 6,520 | 18,300 |
| Expiratory conduit | 32 | 40 | 1,300 | 3,050 | 23,000 |
| | 32 | 42 | 980 | 2,500 | NR |
| | 34 | 42 | 1,100 | 2,540 | NR |
| | 34 | 44 | 1,050 | NR | NR |
| | 36 | 45 | 1,020 | NR | NR |
| | 36 | 46 | 840 | NR | NR |

NR: Conduit outlet T could not be reached
*sequentially heated to this temperature
** calculated from measurement of net gain in weight of conduit These data show that the humidified gas delivery system of the present invention produces less water condensate in each of the inspiratory and expiratory conduits when compared to humidified gas delivery systems of the prior art, across a range of conduit inlet gas temperatures. Also, notably prior arts 1 and 2 were not capable of attaining 44° C. at the expiratory conduit gas outlet.

Example 3

A direct comparative test was undertaken under the following conditions: A humidified gas delivery system according to the present invention and humidified gas delivery systems of the prior art comprising Fisher Paykel model RT200 (Fisher Paykel Healthcare, Auckland, New Zealand) (prior art 1) and Intersurgical model 2026310 (Intersurgical (UK) Limited, Wokingham, UK) (prior art 2) The humidified gas delivery systems were tested using a Maquet Servo 300 ventilator (Maquet Ltd., Sunderland, UK) as ventilation source and heater humidifier model MR850 (Fisher Paykel Healthcare, Auckland, New Zealand) in 'tracheal mode' as heater base and wherein an intervention was made to alter the target temperatures of the humidified gas (see outlet port 40 of FIG. 1) to suit the range of inlet conduit temperatures required for the tests and wherein an intervention was made to ensure that the current supplied to the resistors was interrupted on a ratio of 1:1; typically 5 seconds on and 5 seconds off. This was to mimic the 'in use' scenario whereby target gas temperatures are exceeded and the controller of the heater base switches the current supply off in order for the temperature to reduce to within limits. The following settings and conditions were identical in the systems:

Tidal volume: 500 mL at 21% oxygen;

Respiratory rate: 18 breaths per minute;

Ventilation ratio: I:E 1:2;

PEEP: 5 cmH$_2$O;

Ambient temperature: 21° C. at 30-50% humidity; and

Ambient air speed: <5 cm·s at 1 atmosphere.

The systems were arranged generally in accordance with FIG. 1 (or according to the manufacturer's instructions), and allowed to run for a stabilisation time of approximately 3-hours before the start of the test. Data were recorded at 16-hours after start. Each system was attached to a Maquet 1.0 L patient lung, maintained at 37° C.; and temperatures were measured using a DM509-TX-01 Temperature measurement instrument (Rense Instruments, Oosterhout, NL). A supply of de-ionised water was made available to fill the humidification chamber to maintain its 'auto-fill' level and was sufficient to supply the humidification chamber with water for evaporation for >16 hours. The relevant conduit sub-assemblies of the systems were weighed before the start of the test using an ACB 150 weight measurement instrument (Adam Equipment, Danbury, USA). Measurements were taken in triplicate and the average net weight calculated. The conduits were again weighed at 16-hours after start, in order to establish a difference in weight between the start of the test and the 16-hours caused by accumulation of condensed water along any part of the conduit sub-assembly. Measurements were taken in triplicate and the average net weight gain calculated.

| | Current | Conduit inlet T (° C.) | Present invention ** rain-out (mgH$_2$O) | Prior art 1 ** rain-out (mgH$_2$O) | Prior art 2 ** rain-out (mgH$_2$O) |
|---|---|---|---|---|---|
| Inspiratory conduit | Continuous | 30 | 2,990 | 6,350 | 16,500 |
| | Semi-continuous | 30 | 4,500 | 14,000 | 38,000 |
| | Continuous | 32 | 3,050 | 7,840 | 17,000 |
| | Semi-continuous | 32 | 6,900 | 16,500 | 41,000 |
| | Continuous | 35 | 3,400 | 8,150 | 17,500 |
| | Semi-continuous | 35 | 7,500 | 17,000 | 40,000 |
| | Continuous | 37 | 3,670 | 7,900 | 19,600 |
| | Semi-continuous | 37 | 7,800 | 19,400 | 45,000 |
| | Continuous | 39 | 3,980 | 7,850 | 19,500 |
| | Semi-continuous | 39 | 9,000 | 19,500 | 48,000 |
| Expiratory conduit | Continuous | 32 | 1,300 | 3,050 | 23,000 |
| | Semi-continuous | 32 | 3,400 | 7,000 | 39,500 |
| | Continuous | 34 | 1,100 | 2,540 | 22,500 |
| | Semi-continuous | 34 | 3,600 | 6,550 | 46,500 |
| | Continuous | 36 | 1,020 | 3,500 | 27,000 |
| | Semi-continuous | 36 | 3,550 | 8,100 | 49,000 |

\* sequentially heated to this temperature
\*\* calculated from measurement of net gain in weight of conduit These data show that the humidified gas delivery system of the present invention produces less water condensate in each of the inspiratory and expiratory conduits when compared to humidified gas delivery systems of the prior art, across a range of conduit inlet gas temperatures, when current to the resistors is supplied continuously or semi-continuously.

Example 4

A direct comparative test was undertaken under the following conditions: A humidified gas delivery system according to the present invention and humidified gas delivery systems of the prior art comprising Fisher Paykel model RT200 (Fisher Paykel Healthcare, Auckland, New Zealand) (prior art 1) and Intersurgical model 2026310 (Intersurgical (UK) Limited, Wokingham, UK) (prior art 2) The humidified gas delivery systems were tested using a Maquet Servo 300 ventilator (Maquet Ltd., Sunderland, UK) as ventilation source and heater humidifier model MR850 (Fisher Paykel Healthcare, Auckland, New Zealand) in 'tracheal mode' and 'face mask' mode as appropriate. The following settings and conditions were identical in the systems:

Tidal volume: 500 mL at 21% oxygen;
Respiratory rate: 18 breaths per minute;
Ventilation ratio: I:E 1:2;
PEEP: 5 cmH$_2$O;
Ambient temperature: 21° C. at 30-50% humidity; and
Ambient air speed: <5 cm·s at 1 atmosphere.

The systems were arranged generally in accordance with FIG. 1 (or according to the manufacturer's instructions), and allowed to run for a stabilisation time of approximately 3-hours before the start of the test. Data were recorded at 16-hours after start. Each system was attached to a Maquet 1.0 L patient lung, maintained at 37° C.; and temperatures were measured using a DM509-TX-01 Temperature measurement instrument (Rense Instruments, Oosterhout, NL). A supply of de-ionised water was made available to fill the humidification chamber to maintain its 'auto-fill' level and was sufficient to supply the humidification chamber with water for evaporation for >16 hours. The relevant conduit sub-assemblies of the systems were weighed before the start of the test using an ACB 150 weight measurement instrument (Adam Equipment, Danbury, USA). Measurements were taken in triplicate and the average net weight calculated. The conduits were again weighed at 16-hours after start, in order to establish a difference in weight between the start of the test and the 16-hours caused by accumulation of condensed water along any part of the conduit sub-assembly. Measurements were taken in triplicate and the average net weight gain calculated

|  | Conduit inlet T (° C.) | *Conduit outlet T (° C.) | Present invention  rain-out (mgH$_2$O) | Prior art 1  rain-out (mgH$_2$O) | Prior art 2 ** rain-out (mgH$_2$O) |
|---|---|---|---|---|---|
| Inspiratory conduit | 31 (a) | 34 | 2,990 | 6,600 | 17,250 |
|  | 37 (b) | 40 | 3,450 | 7,900 | 18,800 |
| Expiratory conduit | 34 (a) | 44 | 1,050 | NR | NR |
|  | 34 (b) | 42 | 1,100 | 2,540 | NR |

NR: Conduit outlet T could not be reached
*sequentially heated to this temperature
** calculated from measurement of net gain in weight of conduit These data show that the humidified gas delivery system of the present invention produces less water condensate in each of the inspiratory and expiratory conduits when compared to humidified gas delivery systems of the prior art, across the conduit inlet gas temperatures, used typically in patients without bypassed airways (a) and patients with bypassed airways (b). Notably, the humidified gas delivery system of the prior art was not capable of attaining 44° C. at the expiratory conduit gas outlet.

Example 5

A direct comparative test was undertaken under the following conditions: A humidified gas delivery system according to the present invention and humidified gas delivery systems of the prior art comprising Fisher Paykel model RT200 (Fisher Paykel Healthcare, Auckland, New Zealand) (prior art 1) and Intersurgical model 2026310 (Intersurgical (UK) Limited, Wokingham, UK) (prior art 2) The humidified gas delivery systems were tested using a Maquet Servo 300 ventilator (Maquet Ltd., Sunderland, UK) as ventilation source and heater humidifier model MR850 (Fisher Paykel Healthcare, Auckland, New Zealand) in 'tracheal mode'. The following settings and conditions were identical in the systems:
Tidal volume: 500 mL at 21% oxygen;
Respiratory rate: 18 breaths per minute;
Ventilation ratio: I:E 1:2;
PEEP: 5 cmH$_2$O;
Ambient temperature: 21° C. at 30-50% humidity; and
Ambient air speed: <5 cm·s at 1 atmosphere.

The systems were arranged generally in accordance with FIG. 1 (or according to the manufacturer's instructions), and allowed to run for a stabilisation time of approximately 3-hours before the start of the test. Data were recorded at 16-hours after start. Each system was attached to a Maquet 1.0 L patient lung, maintained at 37° C.; and temperatures were measured using a DM509-TX-01 Temperature measurement instrument (Rense Instruments, Oosterhout, NL). A supply of de-ionised water was made available to fill the humidification chamber to maintain its 'auto-fill' level and was sufficient to supply the humidification chamber with water for evaporation for >16 hours. The surface temperatures of the relevant conduit sub-assemblies of the systems were tested at approximately the middle of the length of the conduit using Fluke 62 Mini IR Thermometer (Fluke (UK) Ltd., Norwich, UK). Measurements were taken in triplicate and the average temperature calculated.

|  | Present invention Conduit outer surface max. T (° C.) | Prior art 1 Conduit outer surface max. T (° C.) | Prior art 2 Conduit outer surface max. T (° C.) |
|---|---|---|---|
| Inspiratory conduit | 35.7 | 34.2 | 32.1 |
| Expiratory conduit | 40.5 | 37.2 | 33.8 |

These data show that the resistors of the humidified gas delivery system of the present invention create higher temperatures on the outer surface of each of the inspiratory and expiratory conduits than when compared to the resistors of the humidified gas delivery system of the prior art.

Example 6

A direct comparative test was undertaken under the following conditions: A humidified gas delivery system according to the present invention and humidified gas delivery systems of the prior art comprising Fisher Paykel model RT200 (Fisher Paykel Healthcare, Auckland, New Zealand) (prior art 1) and Intersurgical model 2026310 (Intersurgical (UK) Limited, Wokingham, UK) (prior art 2) The humidified gas delivery systems were tested using a Maquet Servo 300 ventilator (Maquet Ltd., Sunderland, UK) as ventilation source and heater humidifier model MR850 (Fisher Paykel Healthcare, Auckland, New Zealand) in 'tracheal mode'. The following settings and conditions were identical in the systems:
Tidal volume: 500 mL at 21% oxygen;
Respiratory rate: 18 breaths per minute;
Ventilation ratio: I:E 1:2;
PEEP: 5 cmH$_2$O;
Ambient temperature: 21° C. at 30-50% humidity; and
Ambient air speed: <5 cm·s at 1 atmosphere.

The systems were arranged generally in accordance with FIG. 1 (or according to the manufacturer's instructions), and allowed to run for a stabilisation time of approximately 3-hours before the start of the test. Data were recorded at 16-hours after start. Each system was attached to a Maquet 1.0 L patient lung, maintained at 37° C.; and temperatures were measured using a DM509-TX-01 Temperature measurement instrument (Rense Instruments, Oosterhout, NL). A supply of de-ionised water was made available to fill the humidification chamber to maintain its 'auto-fill' level and was sufficient to supply the humidification chamber with water for evaporation for >16 hours. The surface temperatures of the relevant conduit wires of the systems were tested at approximately the middle of the length of the conduit using Fluke 62 Mini IR Thermometer (Fluke (UK) Ltd., Norwich, UK). Measurements were taken in triplicate and the average temperature calculated.

|  | Present invention Wire surface max. T (° C.) | Prior art 1 Wire surface max. T (° C.) | Prior art 2 Wire surface max. T (° C.) |
|---|---|---|---|
| Inspiratory conduit | 38.3 | 37.1 | 39.5 |
| Expiratory conduit | 47.2 | 44.3 | 38.6 |

These data show that the resistors of the humidified gas delivery system of the present invention create higher temperatures on their surfaces when compared to the resistors of the humidified gas delivery system of the prior art.

Example 7

Figure 8:
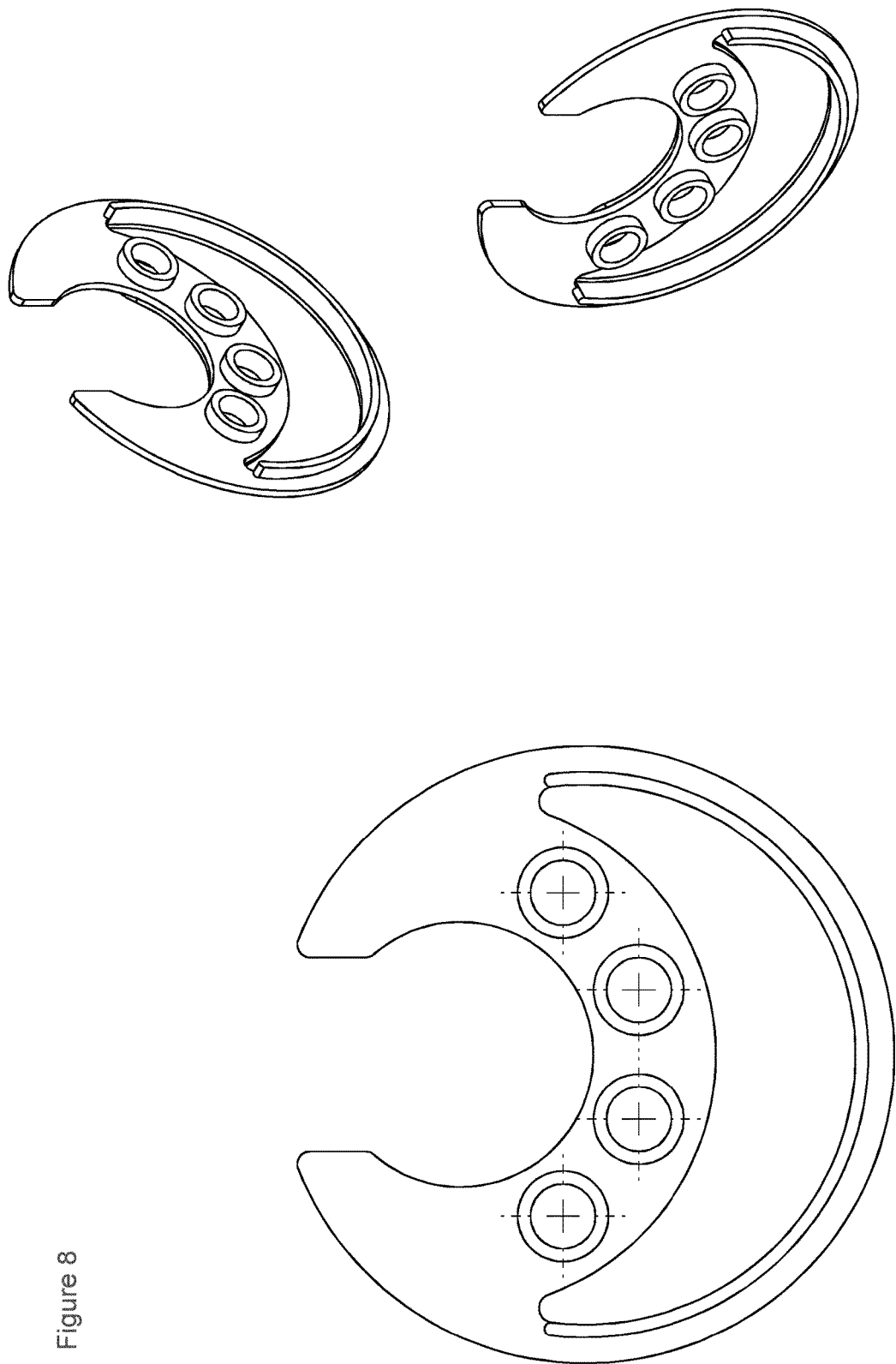
FIG. 8 is a view of an alternative regulating means, which does not form part of the present invention.

A direct comparative test was undertaken under the following conditions: Humidification chambers of a humidified gas delivery system according to the present invention (1a) and a humidification chamber identical in construction to the chamber of the present invention save for absence of any component floating upon the surface of the water to be contained within the chamber (1b) and a chamber identical in construction to the chamber of the present invention save for use of an alternative regulating means similarly positioned at or on the surface of the water to be contained within the chamber (the alternative regulating means; 1c; FIG. 8) were compared in a direct comparative test. The humidified gas delivery systems were tested using a Maquet Servo 300 ventilator (Maquet Ltd., Sunderland, UK) as ventilation source and heater humidifier model MR850 (Fisher Paykel Healthcare, Auckland, New Zealand) in 'tracheal mode' as heater base; and the following settings and conditions were identical in both systems:
Tidal volume: 500 mL at 21% oxygen;
Respiratory rate: 18 breaths per minute;
Ventilation ratio: I:E 1:2;
PEEP: 5 cmH$_2$O;
Ambient temperature: 21° C. at 30-50% humidity; and
Ambient air speed: <5 cm·s at 1 atmosphere.

The systems were arranged generally in accordance with FIG. 1, and allowed to run for a stabilisation time of approximately 3-hours, before the start of the test. Data were recorded at 16-hours after start. Each system was attached to a Maquet 1.0 L patient lung, maintained at 37° C.; and temperatures were measured using a DM509-TX-01 Temperature measurement instrument (Rense Instruments, Oosterhout, NL). A water-containing vessel was primed with de-ionised water with an amount that exceeded the amount required to fill the humidification chamber to its 'auto-fill' level and thought necessary to supply the humidification chamber with water for evaporation for >16 hours. The water-containing vessel, when connected to a feed line connected to the humidification chamber, released water to the humidification chamber until the water fill valving mechanism of the humidification chamber was actuated to cease flow of water to the humidification chamber. The water contained in the humidification chamber was deemed the 'auto-fill' quantity. The water-containing vessel was then valved-off and disconnected from the system prior to being weighed to establish the net weight of remaining water in the water-containing vessel. Weight was calculated using weight measurement instrument (Adam Equipment, Danbury, USA). Measurements were taken in triplicate and the average net weight of water calculated. The water-containing vessel was then reconnected to the water feed line of the humidification chamber and the valved set to open. This provided an open circuit for water to refill the humidification chamber to replace water evaporated by gas flow and heat. The test then started. At 16-hours, the water-containing vessel was again valved-off and disconnected from the system prior to being weighed to establish the net weight of remaining water in the water-containing vessel. Weight was calculated using weight measurement instrument. Measurements were taken in triplicate and the average net weight of water calculated. The difference in weights of water between the start and at 16-hours was quantified in milligrams then divided by the total gas flow passing through the humidification chamber in 16-hours to quantify the milligrams of water evaporated per liter of gas flow flowing through the humidification chamber during 16 hours.

The chamber identical in construction to the chamber of the present invention save for use of an alternative regulating means similarly positioned at or on the surface of the water to be contained within the chamber, herein termed "alternative regulating means" is illustrated in FIG. 8. In the present Example, the alternative regulating means was positioned at the surface of the water within the humidification chamber; specifically at the surface of the water within the humidified gas reservoir of the humidification chamber. The alternative regulating means was adapted to move freely and reciprocally within the humidification chamber, and with the changing level of the water within the humidified gas reservoir. The alternative regulating means comprises six apertures; at least one of which is luniform in shape (crescent-shaped); at least one of which opens at an external edge of the alternative regulating means 44; and four of which are circular apertures. Each of the luniform aperture and four circular apertures further comprises a projection. The projection extends substantially perpendicular from the gas-engaging face of the alternative regulating means (the face of the alternative regulating means, which is in contact with the gas in the humidification chamber). The projection circumscribes at least part of the luniform aperture and each of the four circular apertures. It is thought that the projections act to limit contact of the gas flow in the humidification chamber with the surface of the water as gas flows through the chamber. This alternative embodiment thus limits evaporation potential. The regulating means of the present invention (1a) permits is the water available for evaporation to be 'sitting' level with the top surface of the regulating means, such that the water is in direct contact with the air flow; whereas the alternative regulating means (1c) limits the water available for evaporation by occluding the water from the air flow.

| Ventilation Parameters (I:E 1:2) | 1a AMCA1142 | 1b AMCA1141 | 1c AMCA1142* |
|---|---|---|---|
| Tv700 mL/12RR | 43 | 46 | 37.2 |
| Tv650 mL/15RR | 43.1 | 45.1 | 36.9 |
| Tv600 mL/18RR | 43.2 | 44.3 | 37.8 |
| Tv550 mL/21RR | 43.4 | 40.9 | 37.6 |
| Tv500 mL/24RR | 43.6 | 43.2 | 37.1 |
| Tv450 mL/27RR | 43.1 | 45 | 36.7 |
| Tv400 mL/30RR | 43.2 | 47.1 | 35.8 |
| Tv350 mL/33RR | 43.8 | 47.3 | 34.8 |

AMCA1142 is humidification system from present invention
AMCA1141 is humidification chamber with no regulating means
AMCA1142* is humidification chamber with alternative regulating means These data demonstrate that the regulating means of the present invention produces a level of humidity consistently below 44 mg/H$_2$O than does a humidification chamber having no regulating means; and produces a level of humidity consistently closer to 44 mg/H$_2$O than does a humidification chamber having an alternative regulating means.

The invention claimed is:
1. A humidified gas delivery system comprising at least one conduit defining a lumen and an electrically conductive resistor positioned within the lumen of the conduit; wherein the electrically conductive resistor comprises a wire; and wherein at least part of the wire extends circumferentially within at least a portion of the lumen and at least part of the wire extends diametrically across a transverse cross-section of the lumen.

2. The humidified gas delivery system according to claim 1; wherein the wire is formed from a series of at least two segments, wherein each segment, at least part of the wire is arranged to extend circumferentially within at least a portion of the lumen and at least part of the wire is arranged to extend across a transverse cross-section of the lumen.

3. The humidified gas delivery system according to claim 2; wherein each segment has a serpentine form.

4. The humidified gas delivery system according to claim 2; wherein each segment has a first portion having distal and proximal ends, a middle portion having distal and proximal ends, a second portion having distal and proximal ends, and a connector having distal and proximal ends.

5. The humidified gas delivery system according to claim 4; wherein the first portion is substantially curvilinear in form; the middle portion is substantially linear in form; the second portion is substantially curvilinear in form; and the connector is substantially linear in form.

6. The humidified gas delivery system according to claim 4; wherein the first portion is substantially curvilinear in form, the proximal end of which first portion is connected to the distal end of the middle portion, which middle portion is substantially linear in form; and the proximal end of the middle portion is connected to the distal end of the second portion, which second portion is substantially curvilinear in form; and wherein the connector is substantially linear in form and extends between the distal end of a first portion of a first segment of the wire and the proximal end of a second portion of an adjacent segment of the wire.

7. The humidified gas delivery system according to claim 2; wherein each segment is deformed with respect to the longitudinal axis of the electrically conductive resistor.

8. The humidified gas delivery system according to claim 7; wherein the distal end of a first portion of a first segment of the wire and the proximal end of a second portion of an adjacent segment of the wire are spaced apart with respect to the longitudinal axis of the electrically conductive resistor.

9. The humidified gas delivery system according to claim 7; wherein the wire is formed from a series of at least two segments adjacently arranged with respect to the longitudinal axis of the electrically conductive resistor.

10. The humidified gas delivery system according to claim 1; wherein the wire has a resistivity of about $0.1\times10^{-3}$ Ωm (0.1 milliohmmeters) to about $25.0\times10^{-3}$ Ωm (25.0 milliohmmeters).

11. The humidified gas delivery system according to claim 1; wherein the power dissipated by the wire is from about 18 to about 42 watts.

12. The humidified gas delivery system according to claim 1; wherein the wire has a resistance of about 1.5 to about 3.0 ohms per meter length.

13. The humidified gas delivery system according to claim 1; wherein the wire is formed from a metal or an alloy selected from Aluminum; Brass; Carbon; Constantan; Copper; Iron; Manganin; Molybdenum; Nichrome; Nickel; Platinum; Stainless steel; Steel; Tungsten; and Zinc.

14. The humidified gas delivery system according to claim 1; wherein the at least one conduit comprises a flexible pipe.

15. The humidified gas delivery system according to claim 1; wherein the wire is formed from a series of at least two segments, each segment shaped in the form of a letter S.

16. The humidified gas delivery system according to claim 15; wherein each segment comprises a first end, a middle portion, a second end, and a connector.

17. The humidified gas delivery system according to claim 16; wherein the middle portion of each segment extends diametrically across the transverse cross-section of the lumen.

18. The humidified gas delivery system according to claim 16; wherein the first end and the second end of each segment are connected by the middle portion.

19. The humidified gas delivery system according to claim 16; wherein the connector is oriented in an opposing direction to the middle portion of each segment.

20. The humidified gas delivery system according to claim 19; wherein the connector of each segment extends diametrically across the transverse cross-section of the lumen.

* * * * *